US009235108B2

(12) United States Patent
Mima et al.

(10) Patent No.: US 9,235,108 B2
(45) Date of Patent: Jan. 12, 2016

(54) PROJECTION SYSTEM

(71) Applicant: Panasonic Intellectual Property Management Co., Ltd., Osaka (JP)

(72) Inventors: Kunihiro Mima, Kyoto (JP); Masaaki Nakamura, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 14/640,679

(22) Filed: Mar. 6, 2015

(65) Prior Publication Data

US 2015/0177598 A1 Jun. 25, 2015

Related U.S. Application Data

(63) Continuation of application No. PCT/JP2014/003556, filed on Jul. 3, 2014.

(30) Foreign Application Priority Data

Jul. 5, 2013 (JP) .................................. 2013-141489

(51) Int. Cl.
*G03B 21/14* (2006.01)
*A61B 5/06* (2006.01)
(Continued)

(52) U.S. Cl.
CPC ................. *G03B 21/14* (2013.01); *A61B 5/061* (2013.01); *A61B 19/00* (2013.01); *G06F 3/011* (2013.01);
(Continued)

(58) Field of Classification Search
CPC ........ G03B 21/14; G03B 21/00; G06F 3/011; H04N 9/3194

USPC ................................ 353/28, 121, 122; 606/3
See application file for complete search history.

(56) References Cited

U.S. PATENT DOCUMENTS 5,772,593 A 6/1998 Hakamata
8,610,761 B2* 12/2013 Haisty .................. H04N 9/3147
348/51

(Continued)

FOREIGN PATENT DOCUMENTS

EP 2 540 214 1/2013
JP 09-24053 1/1997

(Continued)

OTHER PUBLICATIONS

International Search Report issued Sep. 22, 2014 in International (PCT) Application No. PCT/JP2014/003556.

*Primary Examiner* — William C Dowling
(74) *Attorney, Agent, or Firm* — Wenderoth, Lind & Ponack, L.L.P.

(57) ABSTRACT

A projection system includes a light source, an imaging unit, a control unit, a storage unit, and a projecting unit. The light source applies light beam having a predetermined wavelength. The imaging unit captures a subject to which the light beam is applied. The control unit generates image data for projection based on the captured image. The storage unit stores plural pieces of figure information each representing image data of an object having a predetermined figure. The projecting unit projects a projection image onto the subject. The control unit selects figure information from the stored figure information, based on a degree of similarity with an image of a captured region responding to the light beam. The control unit generates the image data for projection such that an image including a figure indicated by the selected figure information is projected onto the region responding to the light beam.

8 Claims, 15 Drawing Sheets

(51) Int. Cl.
*A61B 19/00* (2006.01)
*G06T 1/00* (2006.01)
*G06F 3/01* (2006.01)
*H04N 9/31* (2006.01)
*H04N 5/232* (2006.01)
*H04N 5/74* (2006.01)
*A61B 5/00* (2006.01)
*H04N 7/18* (2006.01)

(52) U.S. Cl.
CPC .............. *G06T 1/00* (2013.01); *H04N 5/23293* (2013.01); *H04N 5/7408* (2013.01); *H04N 9/3179* (2013.01); *H04N 9/3194* (2013.01); *A61B 5/744* (2013.01); *A61B 2019/5293* (2013.01); *H04N 7/18* (2013.01)

(56) References Cited

U.S. PATENT DOCUMENTS

| | | | |
|---|---|---|---|
| 8,651,666 B2 * | 2/2014 | Huebner | G03B 21/14 353/28 |
| 2007/0167801 A1 | 7/2007 | Webler et al. | |
| 2008/0004533 A1 | 1/2008 | Jansen et al. | |
| 2010/0177184 A1 | 7/2010 | Berryhill et al. | |
| 2011/0001935 A1 * | 1/2011 | Reale | G03B 21/14 353/28 |
| 2011/0199500 A1 | 8/2011 | Shimizu et al. | |
| 2012/0050688 A1 * | 3/2012 | Wu | G03B 21/26 353/28 |
| 2013/0006178 A1 | 1/2013 | Pinho et al. | |
| 2015/0065921 A1 * | 3/2015 | Enholm | A61N 7/02 601/3 |

FOREIGN PATENT DOCUMENTS

| | | |
|---|---|---|
| JP | 2005-038118 | 2/2005 |
| JP | 2006-180926 | 7/2006 |
| JP | 2009-517177 | 4/2009 |
| JP | 2010-517733 | 5/2010 |
| JP | 2011-167337 | 9/2011 |
| JP | 2012-065698 | 4/2012 |
| JP | 2013-009949 | 1/2013 |
| WO | 2007/067323 | 6/2007 |
| WO | 2008/101129 | 8/2008 |

* cited by examiner

Fig. 5

| NAME OF SURGICAL INSTRUMENTS | FEATURE VALUE a | FEATURE VALUE b | FEATURE VALUE c |
|---|---|---|---|
| CATHETER | a1 | b1 | c1 |
| FORCEPS | a2 | b2 | c2 |
| MERCI | a3 | b3 | c3 |
| ⋮ | ⋮ | ⋮ | ⋮ |

42

(a)

|  | PROJECTION REGION | OUT OF PROJECTION REGION |
|---|---|---|
| FLUORESCENCE EMITTING REGION | NO CHANGE | DISPLAY ADDITIONALLY |
| OUT OF FLUORESCENCE EMITTING REGION | ERASE | NO CHANGE |

(b)

(c)

PROJECTION SYSTEM

TECHNICAL FIELD

This disclosure relates to a projection system that projects a captured image of a subject onto the surface of the subject.

BACKGROUND ART

JP 9-24053 A discloses a surgical operation support system that outputs image data indicating an affected part of a living body to undergo a surgical operation with a fluorescent image imaging apparatus, reproduces an image based on the image data using an image projecting apparatus, and displays the image on the actual affected part. A substance that emits fluorescence by application thereto of a light beam having a predetermined wavelength is administered in advance into the affected part of the living body. The system supports a check on a lesion part by displaying, on the actual affected part, a fluorescent image of the affected part emitting the fluorescence.

SUMMARY OF INVENTION

An object of this disclosure is to provide a projection system for projecting an image that enables a user to recognize more accurately the state of the subject in an image of the subject which is projected on the actual subject.

The projection system according to this disclosure includes a light source, an imaging unit, a control unit, a storage unit, and a projecting unit. The light source applies a light beam having a predetermined wavelength. The imaging unit captures a subject to which the light beam having the predetermined wavelength is applied. The control unit generates image data for projection based on the image captured by the imaging unit. The storage unit stores plural pieces of figure information each representing image data of an object having a predetermined figure. The projecting unit projects a projection image onto the subject based on the image data for projection. The control unit selects a piece of figure information from the plural pieces of figure information stored in the storage unit, based on a degree of similarity with an image of a region responding to the light beam having the predetermined wavelength captured by the imaging unit. The control unit generates the image data for projection such that an image including a figure indicated by the selected piece of figure information is projected onto the region responding to the light beam having the predetermined wavelength.

According to the projection system of this disclosure, the image data for projection is generated by using the piece of figure information selected based on the degree of similarity and, thereby, the image that enables the user to recognize more accurately the state of the subject can be projected.

BRIEF DESCRIPTION OF DRAWINGS

FIG. 5 is a table of an example of feature value data concerning various sorts of surgical instrument;

DESCRIPTION OF EMBODIMENTS

Figure 1:
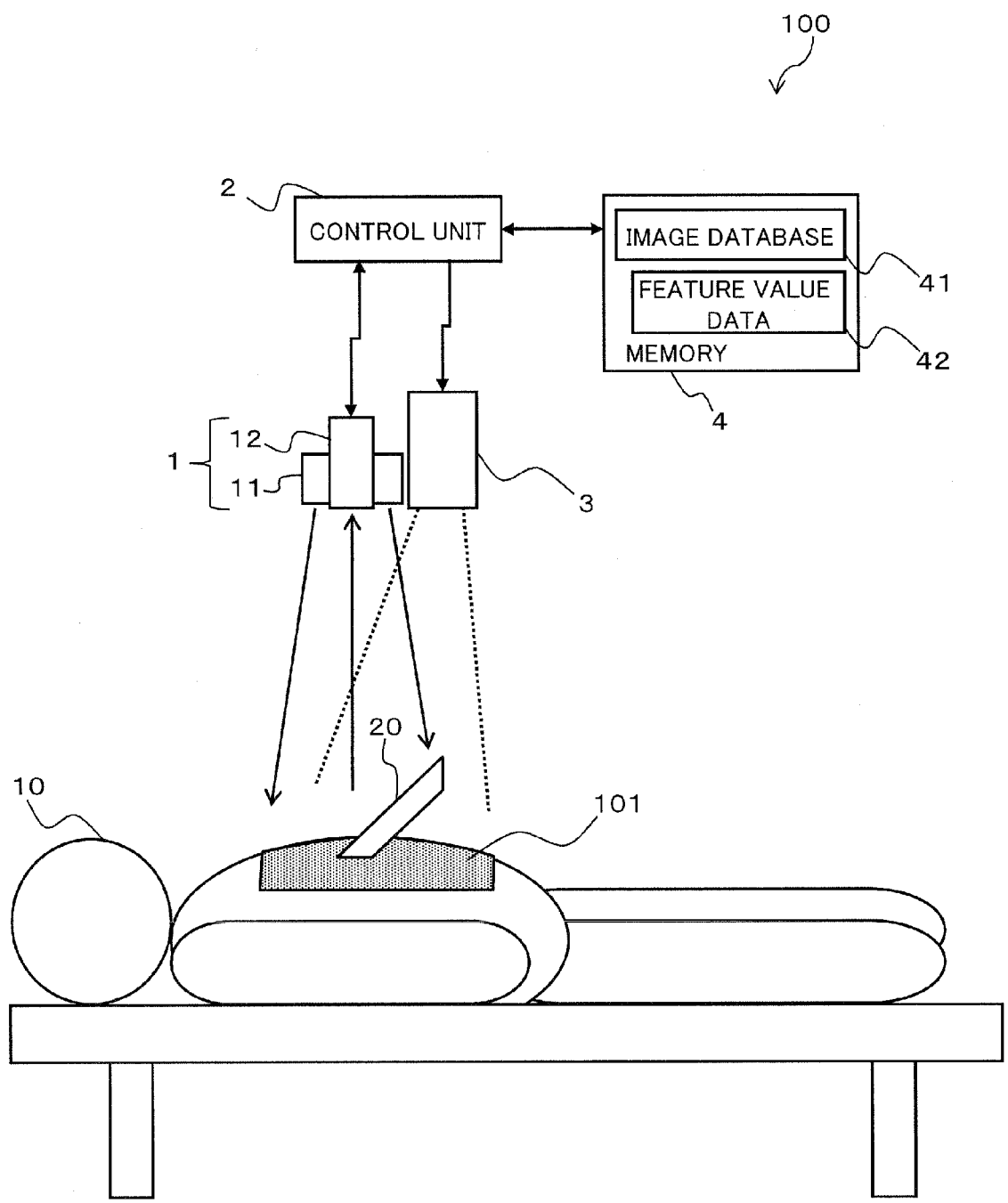
FIG. 1 is a schematic diagram showing a configuration of a medical operation support system according to a first embodiment.

Hereinafter, an embodiment is described in detail while referring to the drawings as appropriate. However, detailed descriptions are sometimes omitted when they are not required. For example, detailed descriptions of already well-known matters and repeated descriptions of substantially identical configurations are sometimes omitted. This has been done in order to avoid the following description from becoming unnecessarily redundant, and to facilitate understanding for persons skilled in the art.

It should be noted that the inventor (s) has provided the appended drawings and the following description in order for persons skilled in the art to sufficiently understand the present disclosure, not with the intention of thereby restricting the subject described in the claims.

(First Embodiment)

A first embodiment will be described with reference to FIGS. 1 to 9.

1-1. Configuration

1-1-1. Overview of Operation Support System

FIG. 1 is a schematic diagram showing a configuration of a medical operation support system according to a first embodiment. The medical operation support system is an example of the projection system.

When a medical operation is preformed, medical devices such as tubes and catheters are inserted into the body of a patient. Usually, the medical devices inserted in the body of the patient cannot be checked by external visual observation. The medical operation support system of this embodiment projects an image representing the figure of a medical instrument onto the surface of a region having the medical instrument inserted therein. Thereby, a user of this operation support system can check the position, etc., of the medical device inserted in the body of the patient.

1-1-2. Configuration of Operation Support System

The configuration of the medical operation support system 100 will be described below in detail.

The medical operation support system 100 includes an imaging apparatus 1, a control unit 2, a projecting unit 3, and a memory 4.

As illustrated in FIG. 1, a medical device 20 is inserted in an operative field 101 of a patient 10 undergoing an operation. The imaging apparatus 1 includes a light source 11 and an imaging unit 12, and captures the operative field 101. The control unit 2 controls each of the components of the medical operation support system 100. The control unit 2 generates image data for projection by executing the processes described later for image data indicating the image captured by the imaging apparatus 1 (captured image data). The projecting unit 3 produces a projection image based on the image data for projection, and projects the projection image onto the operative field 101. The memory 4 has an image database 41 and feature value data 42 stored therein. The details of each of the image database 41 and the feature value data 42 will be described later.

The medical device 20 used in the operation has a photosensitive substance emitting fluorescence by being excited, which is applied on the surface thereof or mixed therein by kneading. The photo-sensitive substance is a substance that is excited and emits fluorescence when, for example, a near-infrared light beam is applied thereto, and is, for example, indocyanine green. The photo-sensitive substance is a medical agent usable for a human body or an animal. The medical device 20 is a capturing target object that is an object to be captured by the imaging apparatus 1.

The light source 11 of the imaging apparatus 1 applies an excitation light beam having a wavelength in an excitation wavelength region for the photo-sensitive substance. For example, the light source 11 applies a light beam of a near-infrared wavelength band. The light source 11 is disposed to surround the imaging unit 12.

The imaging unit 12 includes, for example, a highly sensitive CCD camera. The imaging unit 12 captures a fluorescent image provided by the emission of the fluorescence from the photo-sensitive substance of the medical device 20, and generates the captured image data. The captured image data is image data indicating a fluorescent image of the region emitting the fluorescence, and is output to the control unit 2. The imaging unit 12 captures a visual light image of the operative field 101 together with the fluorescent image. The imaging unit 12 is composed of a camera group including plural cameras in combination each capable of detecting one or plural kind(s) of lights containing, for example, visual light, fluorescence, and excitation light, thereby, to detect all the above kinds of lights. In this embodiment, the imaging unit 12 generates the captured image data that indicates the fluorescent image. The imaging unit 12 may output, to the control unit 2, the data of the overall image acquired as the result of the capturing including the fluorescent image and the visual light image. In this case, the control unit 2 may extract the fluorescent image from the overall image acquired as the result of the capturing.

The control unit 2 has a function of controlling operations of the imaging apparatus 1 and the projecting unit 3. The control unit 2 obtains the captured image data from the imaging apparatus 1, reads figure information (described later) from the memory 4, and executes a predetermined processes described later. Thereby, the control unit 2 generates the image data to be projected from the projecting unit 3 and outputs the image data to the projecting unit 3. The control unit 2 includes, for example, a CPU or an MPU, and realizes its function by executing predetermined programs. The function of the control unit 2 may be realized by an electronic circuit designed for dedicated use thereof.

The projecting unit 3 produces the projection image based on the image data from the control unit 2, and projects the projection image onto the surface of the affected part having the medical device 20 inserted therein, etc. The projecting unit 3 includes, for example, a projector.

The memory 4 is connected to the control unit 2 so that the control unit 2 is able to read the figure information and execute the processes described later. The figure information is the image data indicating the figure of a medical device. Not limiting to the figure of a medical device, the figure information may be the image data of an object having a predetermined figure. The memory 4 is an example of the storage unit. For example, a non-volatile memory or an HDD (Hard Disk Drive) is used as the memory 4.

Figure 2A:
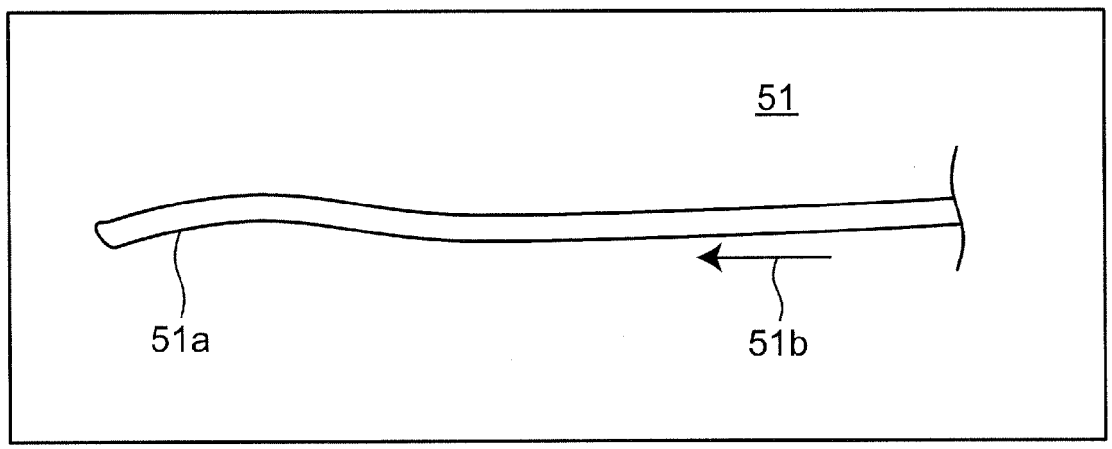
FIG. 2A is a diagram showing an example of image data of a catheter stored in a memory.
Figure 2B:
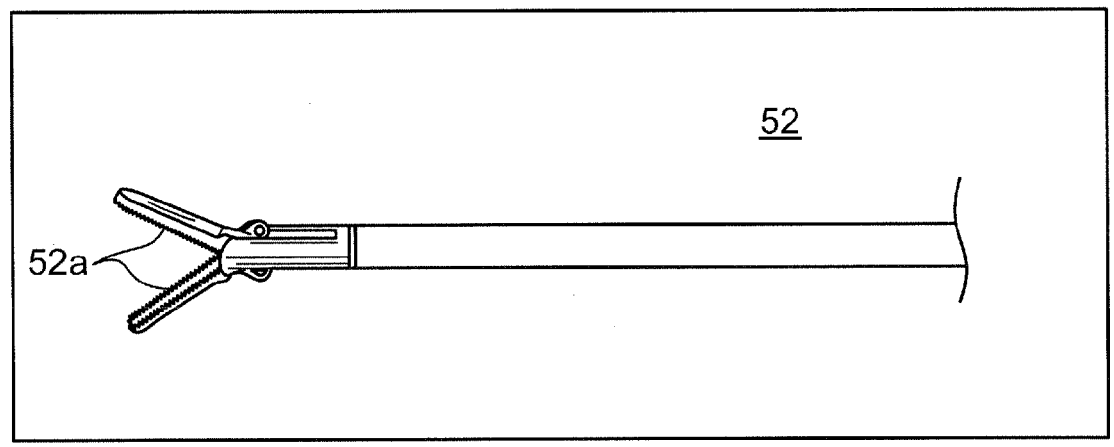
FIG. 2B is a diagram showing an example of image data of forceps stored in the memory.
Figure 2C:
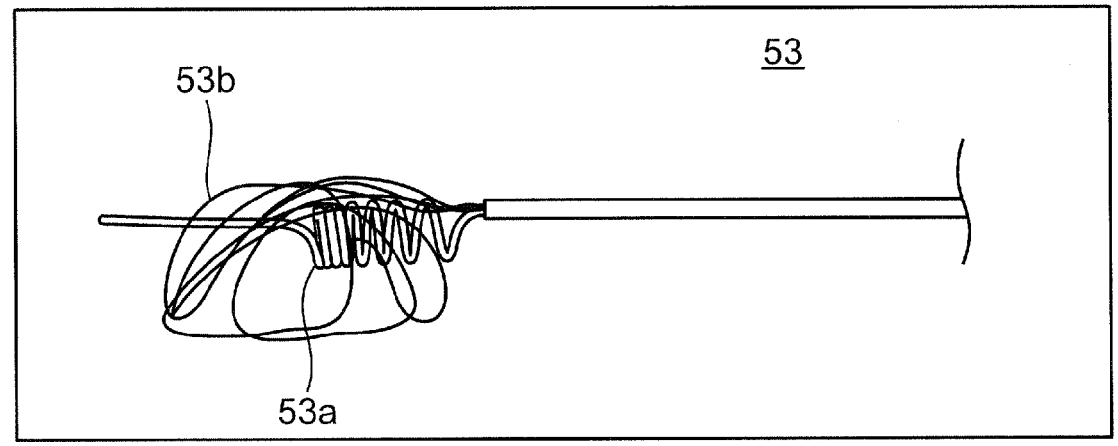
FIG. 2C is a diagram showing an example of image data of a MERCI stored in the memory.

The image data base 41 manages pieces of figure information concerning plural medical devices. FIGS. 2A to 2C show examples of pieces of figure information on plural sorts of surgical instruments included in the image database 41. FIG. 2A shows image data 51 of a catheter. FIG. 2B shows image data 52 of forceps. FIG. 2C shows the image data 53 of a MERCI retriever (hereinafter, referred to as "MERCI"). The pieces of image data 51 to 53 are the examples of the pieces of figure information on the surgical instruments respectively.

The catheter is a tube-shaped surgical instrument to be inserted in the body of the patient 10. One of the features of the image data 51 of the catheter is that the catheter extends to its tip 51a along its longitudinal direction 51b with a constant width.

The forceps are a surgical instrument used to grab or tug an affected part or a suture thread. For example, forceps for an endoscope are used being inserted in the body of the patient 10. One of the features of the image data 52 of the forceps is a bi-forked grabbing unit 52a disposed at the tip thereof.

A MERCI is a surgical instrument inserted in a blood vessel, etc., to remove a thrombus, and includes a loop wire and a filament to tangle and take away the thrombus. One feature of the image data 53 of the MERCI is the helical loop wire 53a disposed at the tip thereof. While the image data 53 of the MERCI has a string-shaped filament 53b, the image database 41 may include the image data 53 of the MERCI without the filament 53b.

The image database 41 includes the pieces of image data of the plural sorts of surgical instrument as shown in FIGS. 2A to 2C, and also includes pieces of image data on the variations of the surgical instruments. The pieces of image data on the variations are pieces of image data each indicating a different figure of each sort of surgical instrument and are, for example, pieces of image data indicating a surgical instrument whose orientations are different from each other, pieces of image data indicating a surgical instrument that is variously deformed, and pieces of image data indicating the same sort of surgical instrument having figures different from each other.

Figure 3:
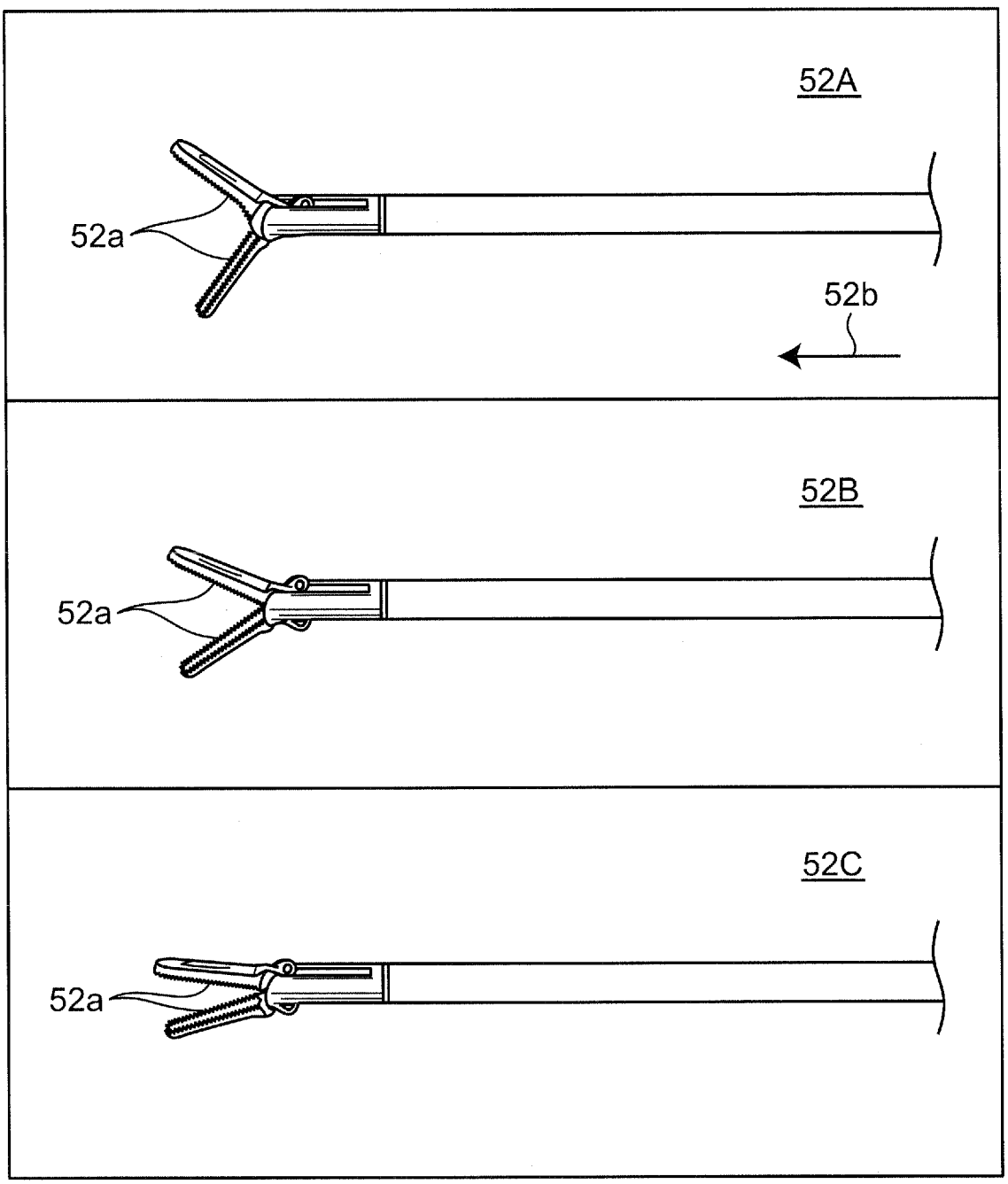
FIG. 3 is a diagram showing examples of pieces of image data of variations of the forceps.

FIG. 3 shows examples of the pieces of image data indicating the variations of the forceps of FIG. 2B. In pieces of image data 52A to 52C of the forceps, the grabbing unit 52a is opened at angles different from each other. The image database 41 may include pieces of image data indicating further variations for the forceps. For example, the image database 41 further includes pieces of image data indicating the variations acquired by rotating the forceps of respective image data 52A to 52C using a longitudinal direction 52b of the forceps as the rotation axis.

Figure 4A:
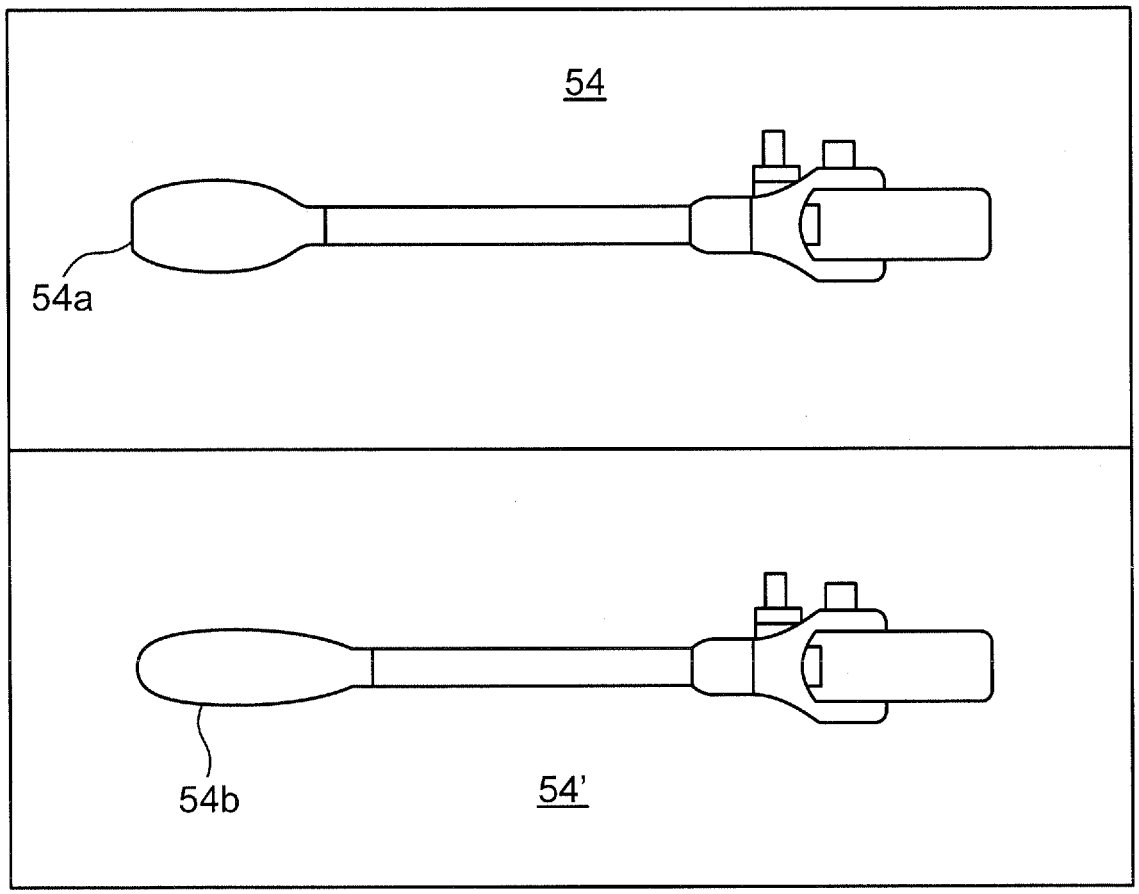
FIG. 4A is a diagram showing examples of pieces of image data of variations of a balloon.
Figure 4B:
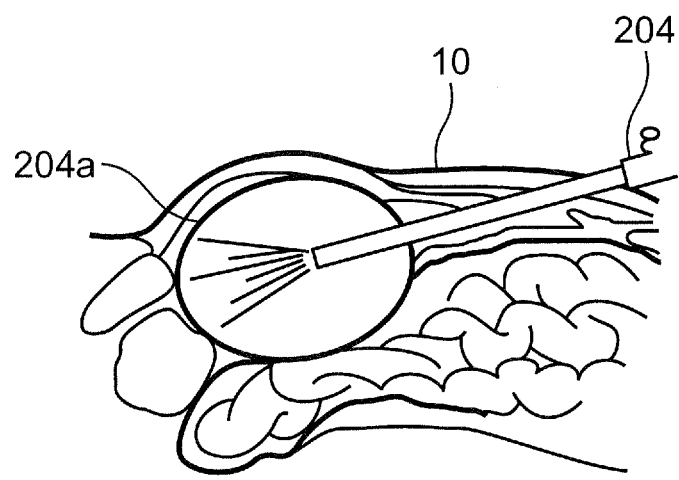
FIG. 4B is a cross-sectional diagram of an affected part for explaining a state of use of the balloon during an operation.

FIG. 4A shows examples of pieces of image data indicating variations of the balloon. The balloon is a surgical instrument used by inflating a tip thereof that is inserted in the body of the patient 10, and another balloon having another figure is used depending on the point of the insertion, etc. As shown in FIG. 4A, the image database 41 includes, for example, image data 54 of a balloon including a tip 54a having an oval figure and image data 54' of a balloon including a tip 54b having an oval figure more flattened in the longitudinal direction than the tip 54a. As shown in FIG. 4B, a tip 204a of an actual balloon 204 is deformed to be expanded in the body of the patient 10 by, for example, an external pump. Corresponding to this, the image database 41 further includes, for example, pieces of image data of variations acquired by deforming the tips 54a, 54b respectively for the pieces of image data 54 and 54' of the balloon.

The feature value data 42 is data indicating a feature values of the surgical instruments of the pieces of figure information included in the image database 41. FIG. 5 shows an example of the feature value data 42 concerning the sorts of surgical instrument of FIGS. 2A to 2C. In FIG. 5, feature values a, b, and c are set for each of the surgical instruments that are the catheter, the forceps, and the MERCI.

For each of the feature values a, b, and c of the surgical instruments, a value is set that represents a feature of a representative figure of each of the surgical instruments in the image database 41. For example, feature values a1, b1, and c1 of the catheter are values extracted from the image data 51. The feature value a is a value representing, for example, the degree of similarity between the figure of each surgical instrument and a tube-shaped figure, and is defined based on the length in the longitudinal direction extending with the constant width in each piece of image data. The feature value b is a value representing, for example, the degree of similarity between the tip of each surgical instrument and a bi-forked figure, and is defined based on the degree of opening of the tip in each piece of image data.

1-2. Operation

An operation of the medical operation support system 100 configured as above will be described.

Figure 6:
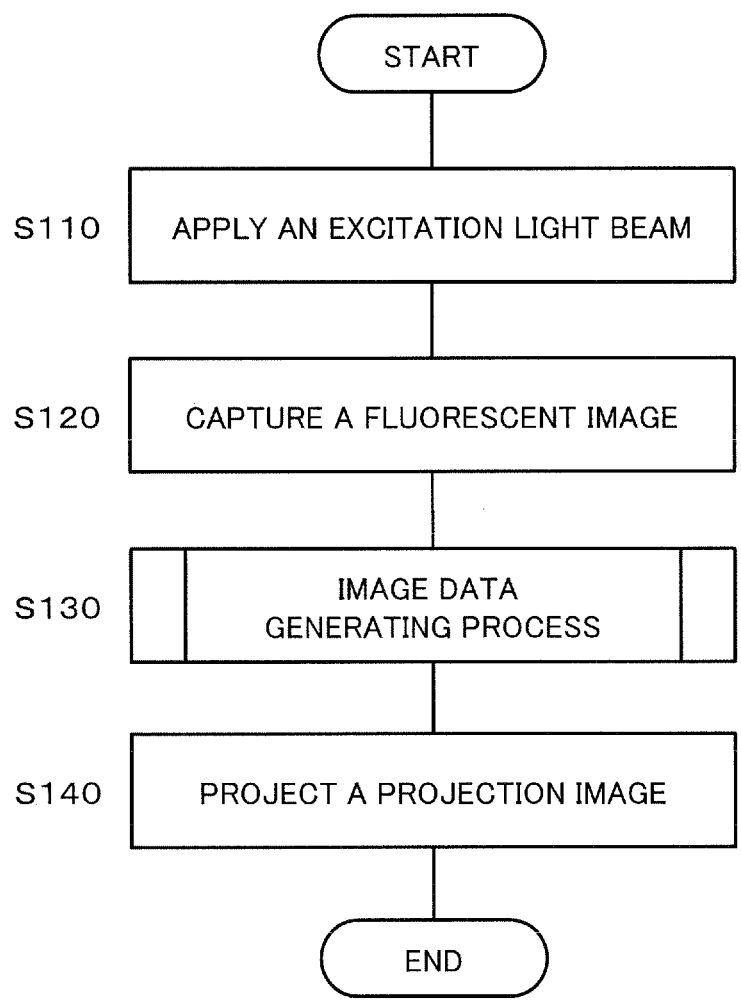
FIG. 6 is a flowchart for explaining a generating process of a projection image in the medical operation support system according to the first embodiment.

FIG. 6 is a flowchart for explaining a generating process of the projection image in the medical operation support system 100.

When a medical operation is performed using the medical operation support system 100 shown in FIG. 1, the imaging apparatus 1 first drives the light source 11 to emit the excitation light beam to the operative field 101 including the medical device 20 (step S110). The excitation light beam from the light source 11 also reaches the medical device 20 inserted in the body of the patient 10. Then, the photo-sensitive substance applied on the surface of the medical device 20 or kneaded therein is excited to emit fluorescence.

Next, the imaging apparatus 1 captures the operative field 101 from the imaging unit 12 (step S120). At this time, the imaging unit 12 detects the fluorescence emitted from the medical device 20 inserted in the body of the patient 10, and generates the captured image data indicating a fluorescent image of the medical device 20. The captured image data is output to the control unit 2.

The control unit 2 performs an image data generating process based on the figure information stored in the memory 4 (step S130). The image data generating process is a process of generating the image data for projection that includes the image of the medical device, such that the image of the medical device corresponding to the fluorescent image of the captured image data is projected onto the operative field 101 (whose details will be described later). The control unit 2 outputs the generated image data to the projecting unit 3.

The projecting unit 3 produces the projection image based on the input image data and projects the produced projection image onto the surface of the operative field 101 (step S140). Thereby, the image presenting the figure of the medical device 20 is displayed at the position at which the medical device 20 is inserted in the operative field 101. The user therefore can visually recognize the position at which the medical device 20 is inserted in the operative filed 101.

The above process is repeatedly executed at predetermined cycles (for example, each 1/60 sec). Thereby, images each capture, for example, every 1/60 sec are projected and the user can visually recognize the position at which the medical device 20 is inserted, as a real time moving image.

Figure 7A:
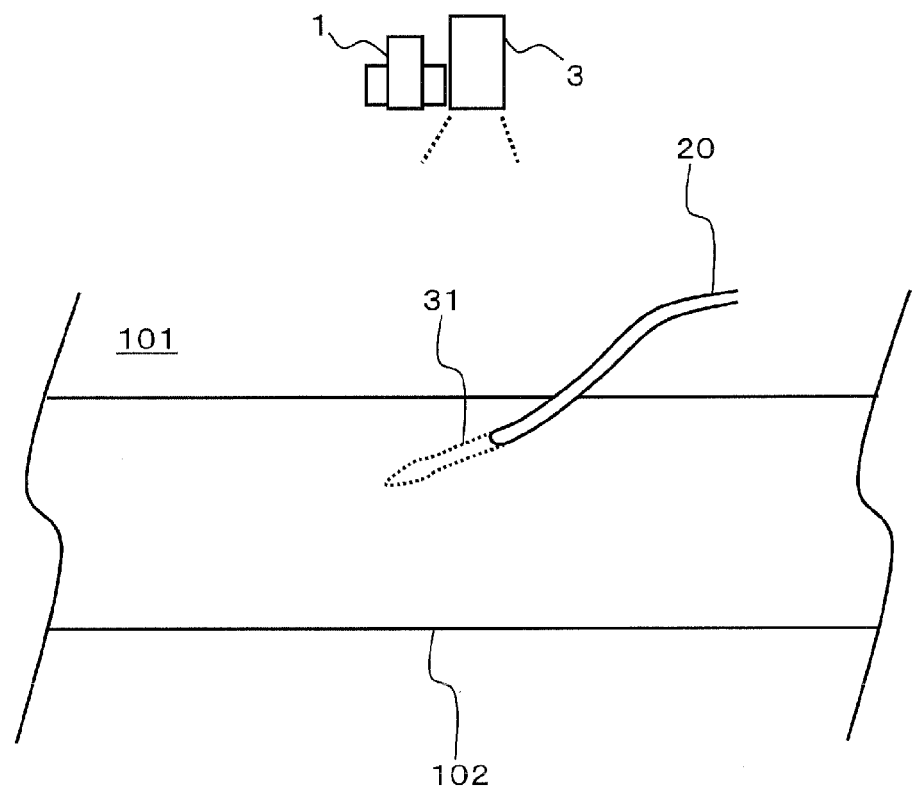
FIG. 7A is a diagram showing an example of a fluorescent image in the generating process of the projection image.

Here, when the emission of the fluorescence is detected from the medical device 20 inserted in the body of the patient 10, the imaging unit 12 detects a light beam transmitted through skin, etc. It is therefore difficult to detect a clear figure of the medical device 20 based on the fluorescent image of the medical device 20. For example, the fluorescent image 31 shown in FIG. 7A presents a blurry image on the surface of the affected part 102 due to the diffusion of the fluorescence emitted from the tip of the medical device 20 in the affected part 102 such as a blood vessel. In this case, if the projecting unit 3 projects an image which is same as the fluorescent image 31, the figure of the region where the medical device 20 is inserted is unclearly displayed.

Further, when plural sorts of medical devices are simultaneously inserted in the body of the patient 10, it is difficult for the user to identify each of the sorts of medical devices.

Figure 7B:
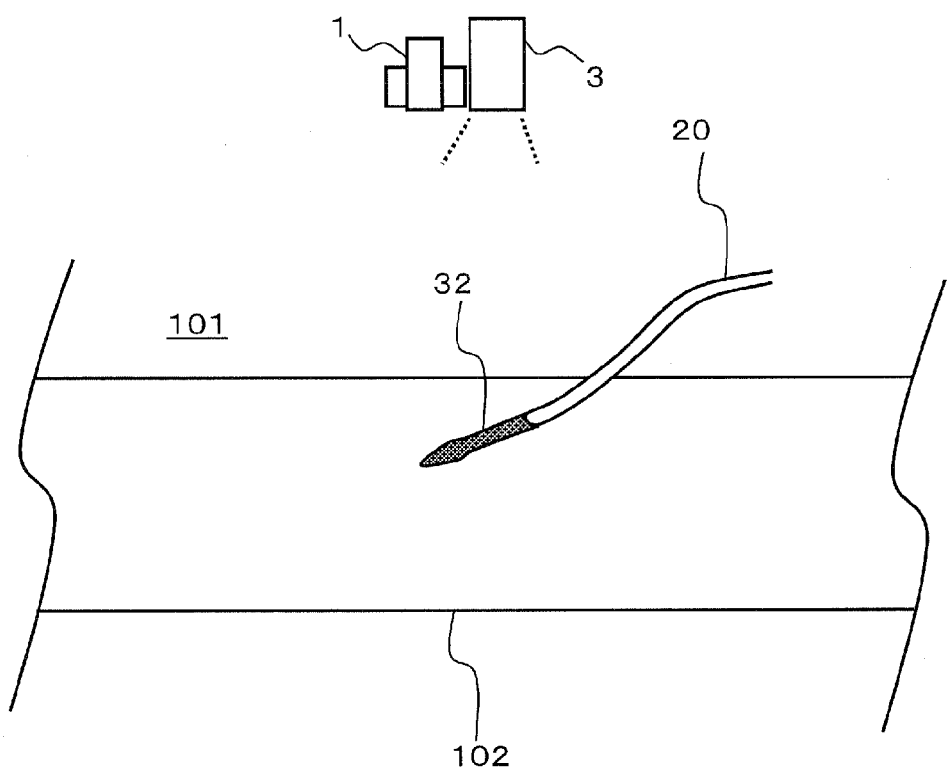
FIG. 7B is a diagram showing an example of the projection image in the generating process of the projection image.

In the image data generating process of this embodiment, therefore, the control unit 2 first compares the figure of the medical device 20 indicated by the captured image data with pieces of figure information on the medical devices stored in the memory 4 and, thereby, determines the actually used medical device. The control unit 2 generates the image data of the projection image by replacing, in the captured image data, the fluorescent image with the figure information on the determined medical device. Thereby, as shown in FIG. 7B, the state (for example, the figure and the sort) can be displayed with clarity of the medical device 20 inserted in the affected part 102 such as a blood vessel using a projection image 32. The comparison between the fluorescent image and the plural pieces of figure information also enables identification of the plural sorts of medical devices.

Alternatively, the control unit 2 may correct the figure of the fluorescent image of the medical device 20 based on the captured image data, according to the figure information on the determined medical device, and may input the corrected image data into the projecting unit 3 as the image data for projection.

1-2-1. Image Data Generating Process

Figure 8:
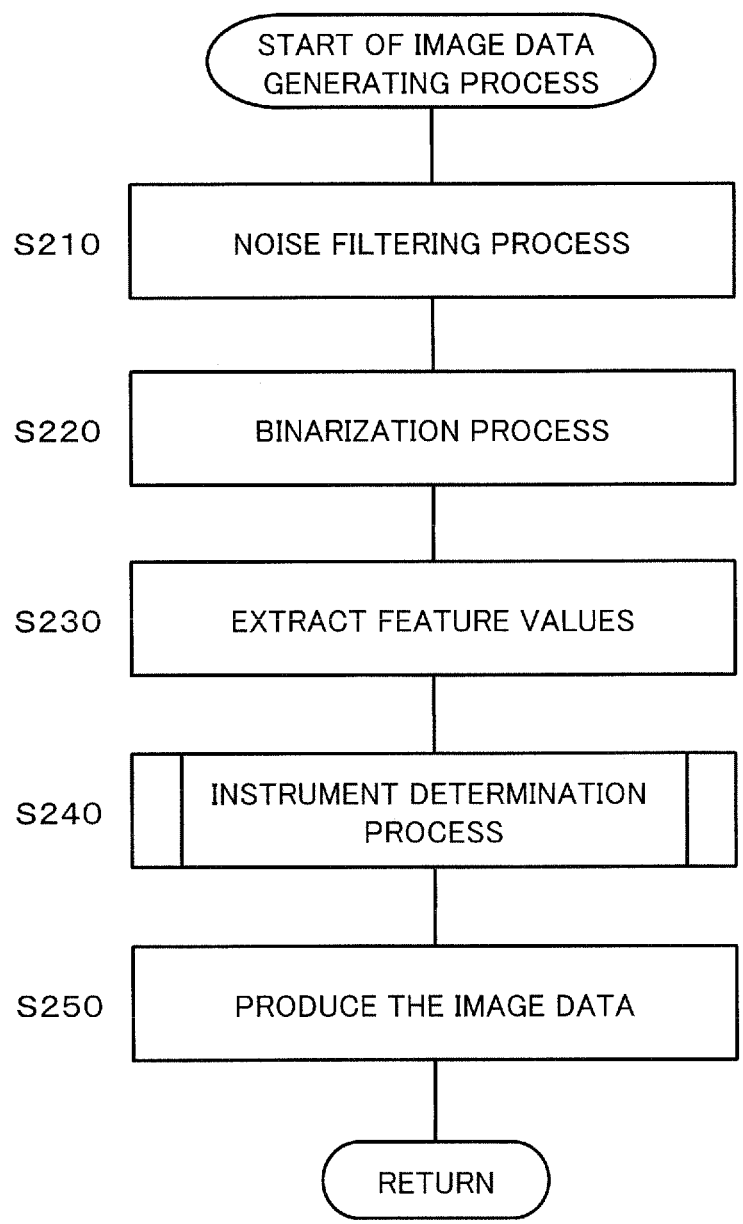
FIG. 8 is a flowchart for explaining an image data generating process in the medical operation support system according to the first embodiment.

The image data generating process in FIG. 6 (step S130) will be described with reference to FIG. 8. FIG. 8 is a flowchart for explaining the image data generating process. In the description, it is assumed that the image data generating process (step S130) starts after the fluorescent image 31 shown in FIG. 7A is captured at step S120 in FIG. 6.

In FIG. 7A, the fluorescent image 31 of the medical device 20 inserted in the affected part 102 such as a blood vessel of the patient 10 is projected on the surface of the affected part 102. As indicated by a dotted line in FIG. 7A, the figure of the fluorescent image 31 is unclear. The figure of the fluorescent image 31 may be unclear because the excited fluorescence beam is diffused by a hypodermal tissue, and so on, depending on the depth of the inserted medical device 20.

The control unit 2 first performs a noise filtering process for the above captured image data (step S210). The noise filtering process is a Gaussian filtering process, and so on, and removes noises in the fluorescent image of the captured image data.

The control unit 2 performs a binarization process (step S220) to clarify the edges of the fluorescent image. The binarization process is performed by, for example, for brightness levels "0" to "255" of each pixel, replacing each of the brightness levels equal to or higher than a predetermined value with the value "255" and, on the other hand, replacing each of the brightness levels lower than the predetermined value with the value "0".

The control unit 2 next extracts the feature values from the binarized fluorescent image (step S230). For example, the control unit 2 first detects the longitudinal direction of the binarized fluorescent image, measures the length of the image in the longitudinal direction extending with the constant width, and, thereby, extracts the value of the feature value a. The control unit 2 additionally extracts the feature value of the tip of the fluorescent image with reference to the detected longitudinal direction.

The control unit 2 performs the instrument determination process based on the extracted feature values (step S240). The instrument determination process is a process of determining the sort of the surgical instrument presented by the fluorescent image, by comparing the feature values extracted from the fluorescent image and the feature values stored in the feature value data 42 of the memory 4 with each other. The details of the instrument determination process will be described later.

Based on the figure information concerning the surgical instrument determined in the instrument determination process (step S240), the control unit 2 generates the image data for the projection image (step S250).

Specifically, the control unit 2 calculates degree of similarity based on the comparison between the feature values of the fluorescent image and the feature values extracted from each piece of figure information. Thereby, the control unit 2 determines the degree of similarity between the captured image data including the fluorescent image of the unclear figure and each piece of figure information stored in the image database 41 concerning the determined medical device. The control unit 2 selects the figure information whose degree of similarity is the highest of the pieces of figure information stored in the memory 4, and determines that the selected piece of figure information is the piece of figure information on the image presenting the state of the medical device actually used in the operation. The control unit 2 generates the image data for projection by replacing the fluorescent image of the captured image data with the image in the figure information which is determined the degree of similarity is the highest.

For example, when the control unit 2 determines in the instrument determination process (step S240) that the surgical instrument presented by the fluorescent image is the forceps, the control unit 2 compares the figure of the fluorescent image with plural pieces of image data 52A to 52C of the forceps shown in FIG. 3, and selects the image data presenting a figure closest to the fluorescent image from the image data 52A to 52C of the forceps. Next, the control unit 2 generates the image data for projection by replacing the fluorescent image in the captured image data with the image in the selected piece of image data.

Additionally, the control unit 2 also detects the state of the medical device 20 such as its size and orientation, based on the captured image data. For example, as the fluorescent image of the medical device 20 inserted in the affected part 102 often presents a device that has a substantially tube-like shape and that has a feature at its tip (see FIG. 7A), its state may be detected for its orientation with reference to the longitudinal direction of the fluorescent image. The control unit 2 performs, for the image data determined the degree of similarity is the highest, a process of adjusting the magnification ratio of enlarging or shrinking and a rotation angle therefor to match with the detected size and orientation. The control unit 2 causes the position of the fluorescent image that is the region emitting the fluorescence on the surface of the affected part and the position of the projection image, to be aligned with each other in the captured image data.

After the control unit 2 generates the image data for projection, the control unit 2 causes the image data generating process to come to an end.

The instrument determination process of step S240 in FIG. 8 will be described. In the instrument determination process, the control unit 2 reads the feature value data 42 from the memory 4, compares the feature values of each of the surgical instruments in the feature value data 42 and the feature values of the fluorescent image extracted in the process of step S230 with each other, and, thereby, determines the sort of the surgical instrument in the captured image data. The instrument determination process will be described with reference to FIGS. 5 and 9.

Figure 9:
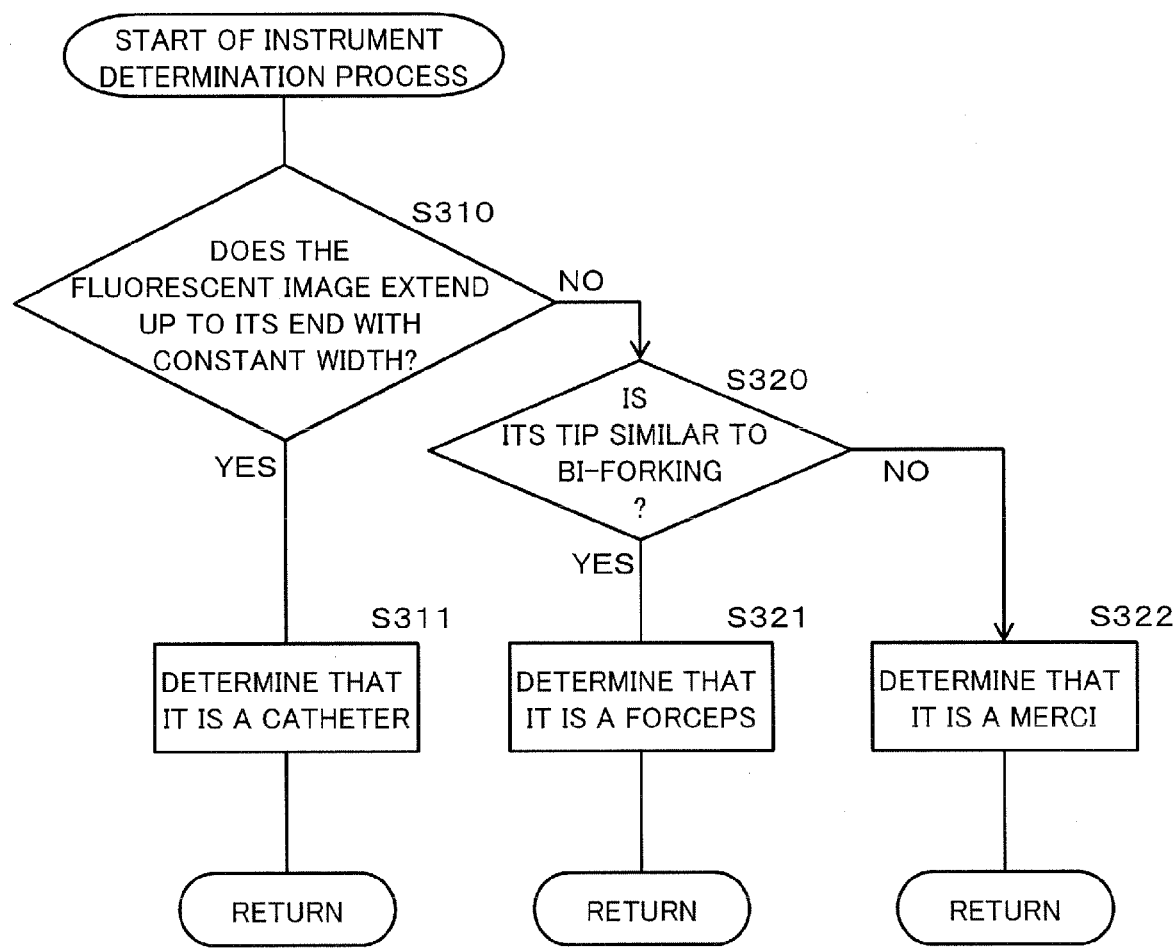
FIG. 9 is a flowchart for explaining an example of an instrument determination process in the medical operation support system according to the first embodiment.

FIG. 9 is a flowchart for explaining an example of the instrument determination process. In the example of FIG. 9, it is assumed as an example that the control unit 2 determines which one of the catheter, the forceps, and the MERCI the surgical instrument presented by the captured image data is, based on the feature value data 42 of FIG. 5.

The control unit 2 determines whether the fluorescent image extends up to its tip with the constant width or not, to compare the fluorescent image with the catheter (step S310). This determination is performed by determining, for example, whether the feature value a exceeds a predetermined threshold value or not. When the control unit 2 determines that the fluorescent image extends up to its tip with the constant width (YES at step S310), the control unit 2 determines that the surgical instrument in the fluorescent image is the catheter (step S311).

On the other hand, when the control unit 2 determines that the fluorescent image does not extend up to its tip with a constant width (YES at step S320), the control unit 2 compares the feature values of the tip figure of the fluorescent image and the feature values of the surgical instrument other than the catheter in the feature value data 42 with each other. For example, the control unit 2 determines whether the tip of the fluorescent image is similar to the bi-forking (step S320). When the control unit 2 determines that the tip in the fluorescent image is similar to the bi-forking (YES at step S320), the control unit 2 determines that the surgical instrument is the forceps (step S321). On the other hand, when the control unit 2 determines that the tip of the fluorescent image is not similar to the bi-forking (NO at step S320), the control unit 2 determines that the surgical instrument is a MERCI (step S322).

After the control unit 2 determines the sort of the surgical instrument in the fluorescent image, the control unit 2 terminates the instrument determination process. The sorts of surgical instrument determined in the instrument determination process are not limited to a combination of the catheter, the forceps, and the MERCI. For example, the control unit 2 may determine whether the fluorescent image presents the balloon, by detecting the feature values concerning the inflation of the tip presented by the fluorescent image.

With the instrument determination process, the sort of the surgical instrument presented by the fluorescent image can be determined based on the feature values stored in advance in the feature value data 42 and the throughput of the control unit 2 can therefore be reduced.

With the image data generating process (step S130), as shown in FIG. 7B, the projection image 32 based on the image data for projection is projected from the projecting unit 3, onto the region emitting the fluorescence on the surface of the affected part 102 (step S140). Performing of the above processes enables clear display of the image of the medical device 20 on the affected part 102.

Although the imaging unit 12 is configured to be able to detect both of the visual light and the fluorescence in this embodiment, the system may be configured to include an imaging unit to detect only the visual light and an imaging unit to detect only the fluorescence separately from each other for performing the above processes. Thereby, the fluorescent image of the medical device 20 and the projection image from the projecting unit 3 can be detected separately from each other. As a result, the degree of similarity can be determined by comparing only the fluorescent image and the pieces of figure information stored in the memory 4 with each other. Thus the provision of the imaging units separately from each other improves the determination precision of the degree of similarity.

1-3. Effects and the Like

As above, in this embodiment, the medical operation support system 100 includes the light source 11, the imaging unit 12, the control unit 2, the memory 4, and the projecting unit 3. The light source 11 applies the excitation light beam having the predetermined wavelength. The imaging unit 12 captures the medical device 20 in the operative field 101 that is the subject to which the excitation light beam is applied. The control unit 2 generates the image data for projection based on the captured image data captured by the imaging unit 12. The memory 4 stores the plural data groups each including the plural pieces of figure information each indicating the figure of the image of the medical device. The projecting unit 3 projects the projection image based on the image data for projection, onto the operative field 101. The control unit 2 selects the piece of figure information based on the degree of similarity to the fluorescent image that is the image of the region responding to the excitation light beam and emitting fluorescence, captured by the imaging unit 12, from the plural pieces of figure information stored in the memory 4. The control unit 2 generates the image data for projection such that the image including the figure indicated by the selected piece of figure information is projected onto the region emitting the fluorescence of the operative field 101.

According to the above configuration, even when the fluorescent image of the medical device 20 inserted in the body of the patient is unclear due to the influence of skin, etc., the medical operation support system 100 can determine the used medical device 20 by comparing the fluorescent image and the pieces of figure information on the medical devices with each other. The medical operation support system 100 can project, onto the surface of the affected part, a moving image of the medical device 20 with its position, its size, and its orientation clear and accurate, based on the image data for projection generated by using the pieces of figure information. The image can therefore be projected with which a doctor, etc., can more accurately recognize the state of the subject.

As above, the medical operation support system 100 of the first embodiment can facilitate the understanding by the user of the state of the medical device such as its sort and its position in the projection image to be projected onto the actual affected part into which the medical device is inserted.

(Second Embodiment)

A second embodiment will be described with reference to FIGS. 10 to 15C. Whereas the image of the medical device inserted in the body of the patient is projected in the first embodiment, an image of a lesioned affected part of a patient is projected in this embodiment.

2-1. Configuration 2-1-1. Overview of Medical Operation Support System

Figure 10:
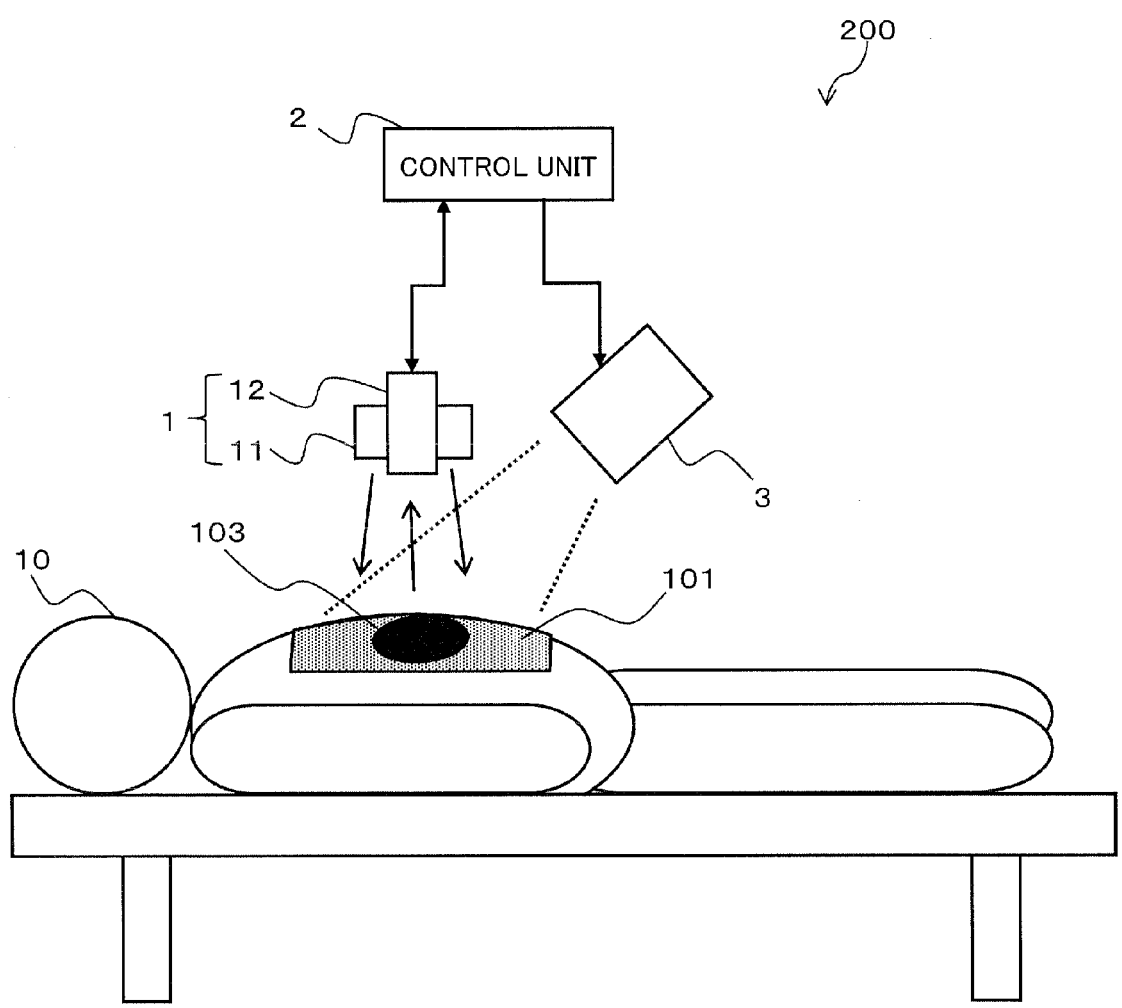
FIG. 10 is a schematic diagram showing a configuration of a medical operation support system according to a second embodiment.

FIG. 10 is a schematic diagram showing a configuration of a medical operation support system according to the second embodiment. The medical operation support system is an example of the projection system.

The medical operation support system according to this embodiment captures a fluorescent image of the affected part in the operative field, detects a region emitting fluorescence of the affected part from the captured image, and projects a projection image using the visual light onto the region of a subject corresponding to the detected region. Thereby, a user of this medical operation support system can recognize the position, and so on, of the affected part of the patient by visual observation.

In this case, if the region of the projection image projected onto the affected part and the region of the affected part emitting the fluorescence in the operative field are deviated from each other, a problem arises that the position of the affected part is wrongly recognized. The medical operation support system according to this embodiment thus captures the fluorescent image of the affected part and the projection image projected onto the affected part, detects the difference therebetween, corrects the projection image, and, thereby, resolves the shift of the projection image. Accordingly, the user (such as a doctor) can correctly check the region of the affected part of the patient.

The medical operation support system 200 will be described without arbitrarily again describing the configurations and operations same as those of the medical operation support system 100 according to the first embodiment.

2-1-2. Configuration of Medical Operation Support System

The configuration of the medical operation support system 200 will be described in detail with reference to FIG. 10.

Similarly to the medical operation support system 100 according to the first embodiment, the medical operation support system 200 according to this embodiment includes the imaging apparatus 1, the control unit 2, and the projecting unit 3 but does not include the memory 4 including the pieces of figure information on the medical devices.

For the patient 10 undergoing the medical operation, the photo-sensitive substance emitting the fluorescence by excitation by the light beam having the predetermined wavelength (the excitation light beam) is administered in advance in the blood, the lymph fluid, and so on, therein, and the photo-sensitive substance is accumulated in an affected part 103 where flows of the blood and the lymph fluid are blocked therein. The photo-sensitive substance is a substance that is excited and emits the fluorescence when, for example, a near-infrared light beam is applied thereto, and is, for example, indocyanine green. The affected part 103 having the photo-sensitive substance accumulated therein emits the fluorescence by the application of the excitation light beam from the light source 11.

In this embodiment, in the operative field 101, the imaging unit 12 captures the fluorescent image by the fluorescent emission from the photo-sensitive substance of the affected part 103 and a visual light image by the visual light, to generate the captured image data. The captured image data is therefore a piece of image data that includes not only the fluorescent image of the region emitting the fluorescence but also the visual light image thereof by the visual image.

2-2. Operation

An operation of the medical operation support system 200 configured as above will be described.

Figure 11:
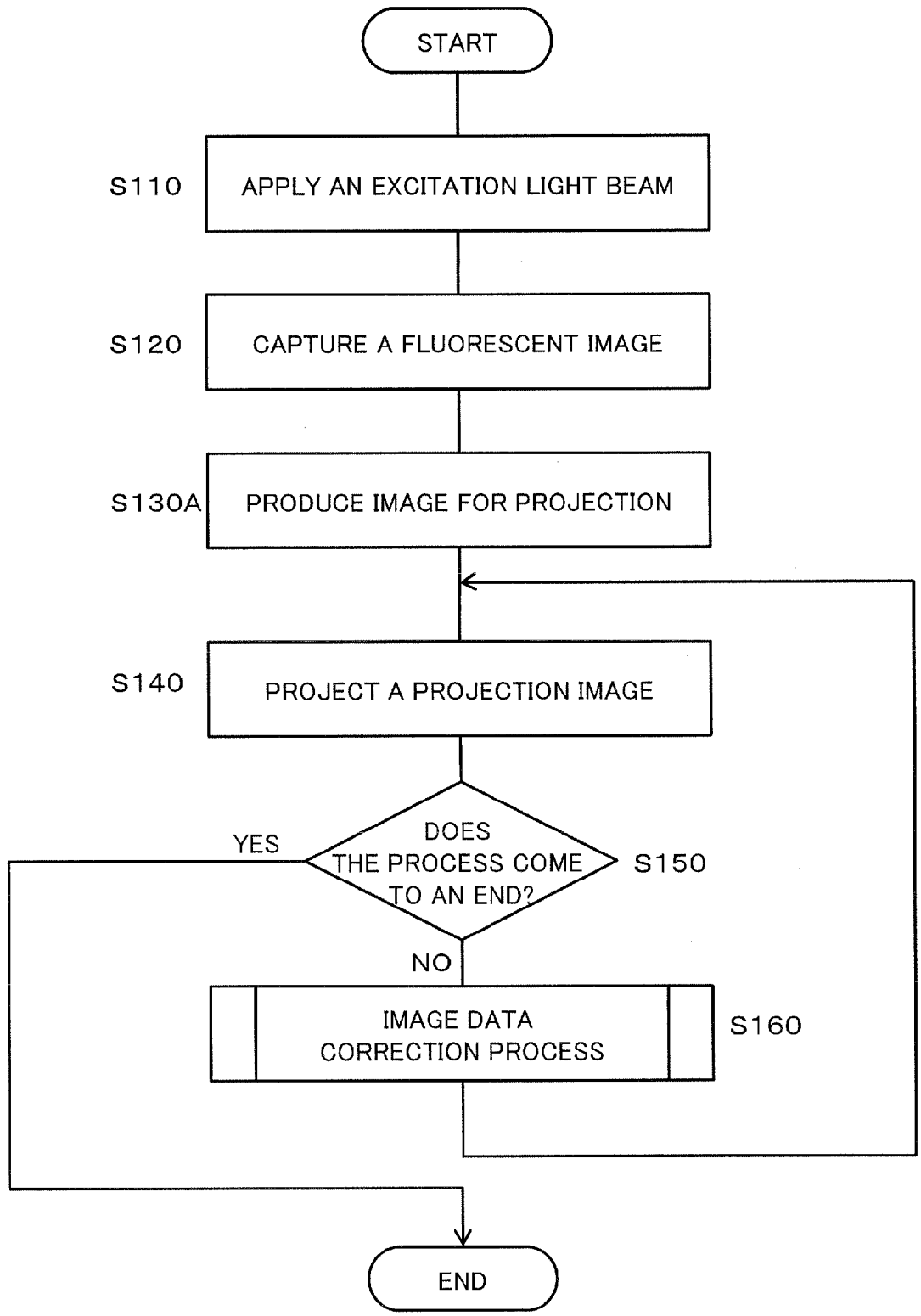
FIG. 11 is a flowchart for explaining a generating process of a projection image according to the second embodiment.

FIG. 11 is a flowchart for explaining a generating process of the projection image in the medical operation support system 200.

First, the imaging apparatus 1 drives the light source 11 to emit the excitation light beam to the operative field 101 including the affected part 103 (step S110). The excitation light beam from the light source 11 excites the photo-sensitive substance accumulated in the affected part 103 of the patient 10 so that the affected part 103 emits the fluorescence.

Next, the imaging apparatus 1 captures the operative field 101 from the imaging unit 12 (step S120). At this time, the imaging unit 12 generates the captured image data that indicates the visual light image of the operative field 101 together with the fluorescent image by the photo-sensitive substance accumulated in the affected part 103. The captured image data is output to the control unit 2.

The control unit 2 generates the image data for projection based on the captured image data (step S130A). In this embodiment, the control unit 2 extracts the fluorescent image of the affected part 103 from the captured image data, and generates the image data for projection to display the projection image presenting the figure of the extracted fluorescent image by using the visual light. The control unit 2 outputs the image data for projection to the projecting unit 3.

The projecting unit 3 projects the projection image presenting the figure of the affected part 103 in the region emitting the fluorescence on the surface of the affected part 103 (step S140). The doctor, and so on, can clearly and visually recognize the position and the figure of the affected part 103 in the operative field 101 by using the projection image.

The control unit 2 performs an image data correction process (step S160). The image data correction process is a process of detecting the projection image actually projected onto the operative field 101 and the fluorescent image, and correcting the image data for projection (the details thereof will be described later). The image data for projection corrected by the control unit 2 is again output to the projecting unit 3. The projecting unit 3 projects the projection image based on the corrected image data for projection, onto the affected part 103 of the operative field 101 (step S140)

The above process is repeatedly performed at the predetermined cycles (for example, each 1/60 sec) until an operation is performed to cause the process to come to an end (step S150). Thereby, images each capture, for example, once every 1/60 sec are projected and the user can visually recognize the position and the figure of the affected part 103 as a real time moving image.

2-2-1. Image Data Correction Process

The details of the image data correction process (step S160) will be described.

In the above generating process of the projection image, deviation may arise between the position of the actual affected part 103 and the position at which the projection image by the projecting unit 3 is projected, caused by the difference of the disposed position between the imaging apparatus 1 and the projecting unit 3. The deviation also arises between the actual position of the affected part 103 and the position at which the projection image is projected due to the surface figure of the affected part 103 or a move of the affected part 103.

Figure 12A:
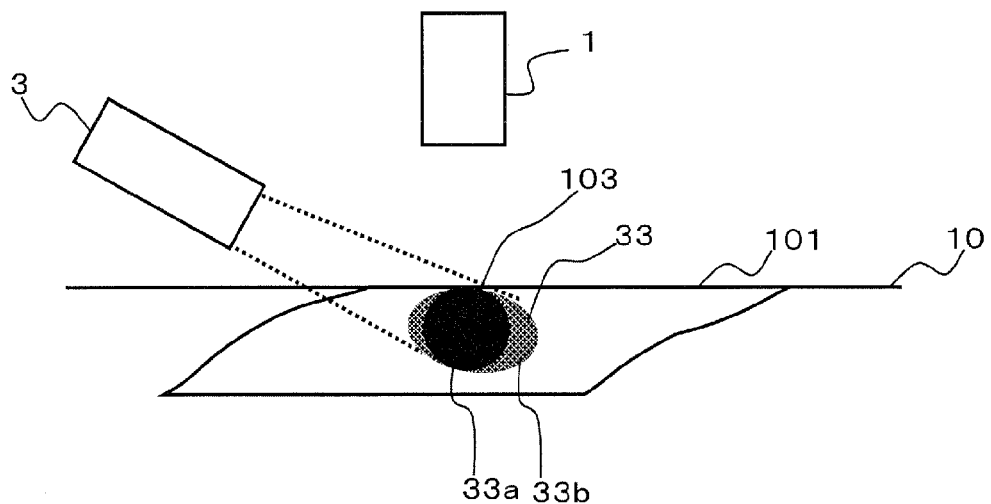
FIG. 12A is a diagram showing an example of the projection image of the medical operation support system according to the second embodiment.
Figure 12B:
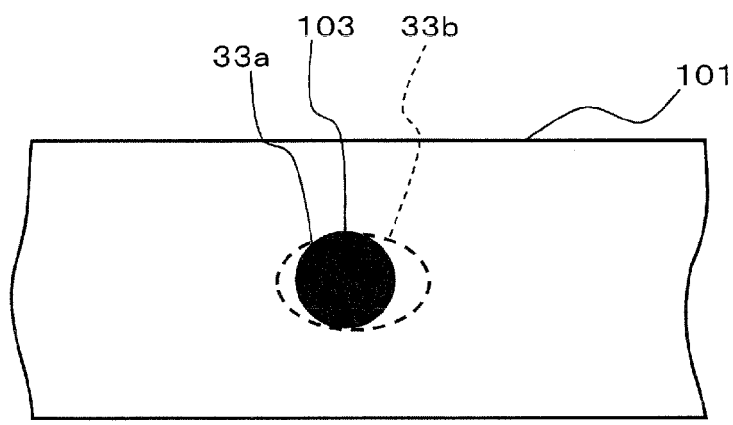
FIG. 12B is a diagram showing exemplary display of the projection image based on an image data correction process of the second embodiment.
Figure 12C:
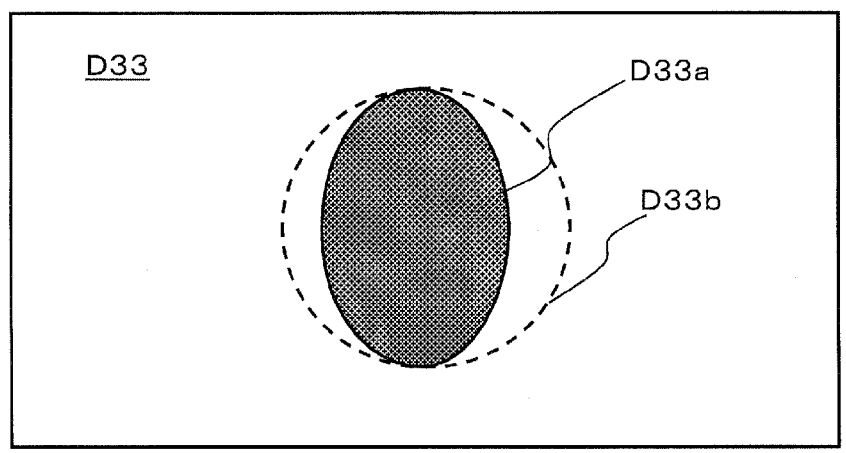
FIG. 12C is a diagram showing an example of image data for projection in the image data correction process of the second embodiment.

FIGS. 12A to 12C show exemplary display by the medical operation support system 200 acquired when the imaging apparatus 1 and the projecting unit 3 are disposed at positions different from each other. In the example shown in FIGS. 12A to 12C, the imaging apparatus 1 is disposed facing the affected part 103 above the operative field 101. On the other hand, the projecting unit 3 is disposed facing the affected part 103 inclined against the operative field 101.

It is assumed in the example of FIGS. 12A to 12C that the figure of the affected part 103 has a circular shape. A region 33a where the affected part 103 emitting the fluorescence and a projection image 33 are overlapped with each other is represented by a blackened region. In this case, the imaging apparatus 1 captures a circular fluorescent image. The control unit 2 generates a piece of image data for projection that indicates a circular projection image. FIG. 12A shows the state where the control unit 2 outputs the image data for projection without making any correction thereto, to the projecting unit 3. Because the projecting unit 3 is disposed inclined against the operative field 101, the projection image 33 actually projected onto the operative field 101 is an oval image. The affected part 103 and the projection image 33 are deviated from each other as shown in FIG. 12A.

The medical operation support system 200 of this embodiment performs the image data correction process (step S160) to correct the deviation between the images. Specifically, the control unit 2 detects the difference between the fluorescent image of the affected part 103 and the projection image 33 and corrects the image data for projection corresponding to the difference (see FIG. 12C). For example, as shown in FIG. 12B, the medical operation support system 200 erases a region 33b spreading outside the affected part 103 keeping the region 33a displayed of the projection image that matches with the affected part 103. The deviation of the projection image 33 can therefore be reduced and the region of the affected part 103 can more accurately be presented. The throughput of the control unit 2 can be reduced by correcting the image data for projection corresponding to the detected difference.

Figure 13:
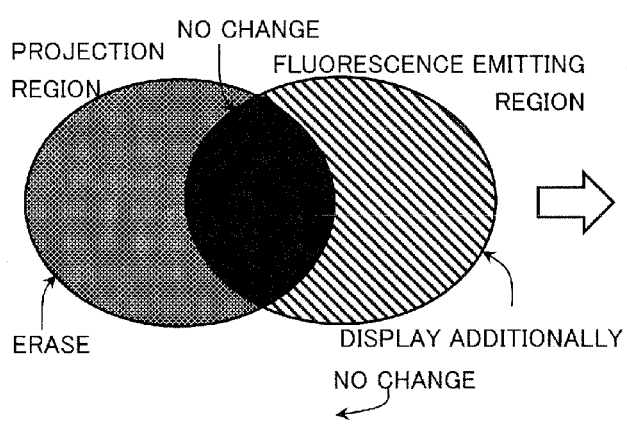
FIG. 13 is a diagram for explaining the thought of correction of the image data for projection in the medical operation support system of the second embodiment.
Figure 13:
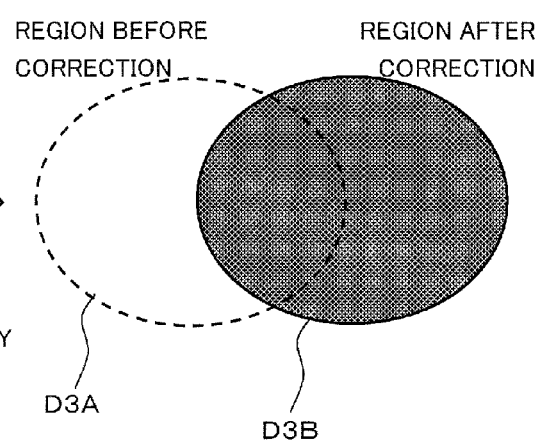

The thought of the correction in the image data correction process will be described. FIG. 13 is a diagram for explaining the thought of the correction of the image data for projection. In the image data correction process, the control unit 2 corrects the image data for projection based on the overlapping of regions in the operative field 101, of the region emitting the fluorescence (hereinafter, referred to as "fluorescence emitting region") and the region onto which the projection image is projected (hereinafter, referred to as "projection region").

The control unit 2 does not change and maintains the image data for projection for the region having the fluorescence emitting region and the projection region overlapped therein on each other (a left column in the top row of FIG. 13(a)).

The control unit 2 corrects the image data for projection for the fluorescence emitting region that does not overlap on the projection region so that the projection image is additionally displayed (a right column in the top row of FIG. 13(a)).

The control unit 2 corrects the image data for projection for the projection region that does not overlap on the fluorescence emitting region so that the projection image is erased (a left column in the bottom row of FIG. 13(a)).

The control unit 2 does not change the image data for projection for a region that is neither the fluorescence emitting region nor the projection region (a right column in the bottom row of FIG. 13(a)).

For example, when the projection region and the fluorescence emitting region are in the state as shown in FIG. 13(b), performing of the above processes causes the image data for projection to be corrected from a region D3A before the correction to a region D3B after the correction as shown in FIG. 13(c).

Figure 14:
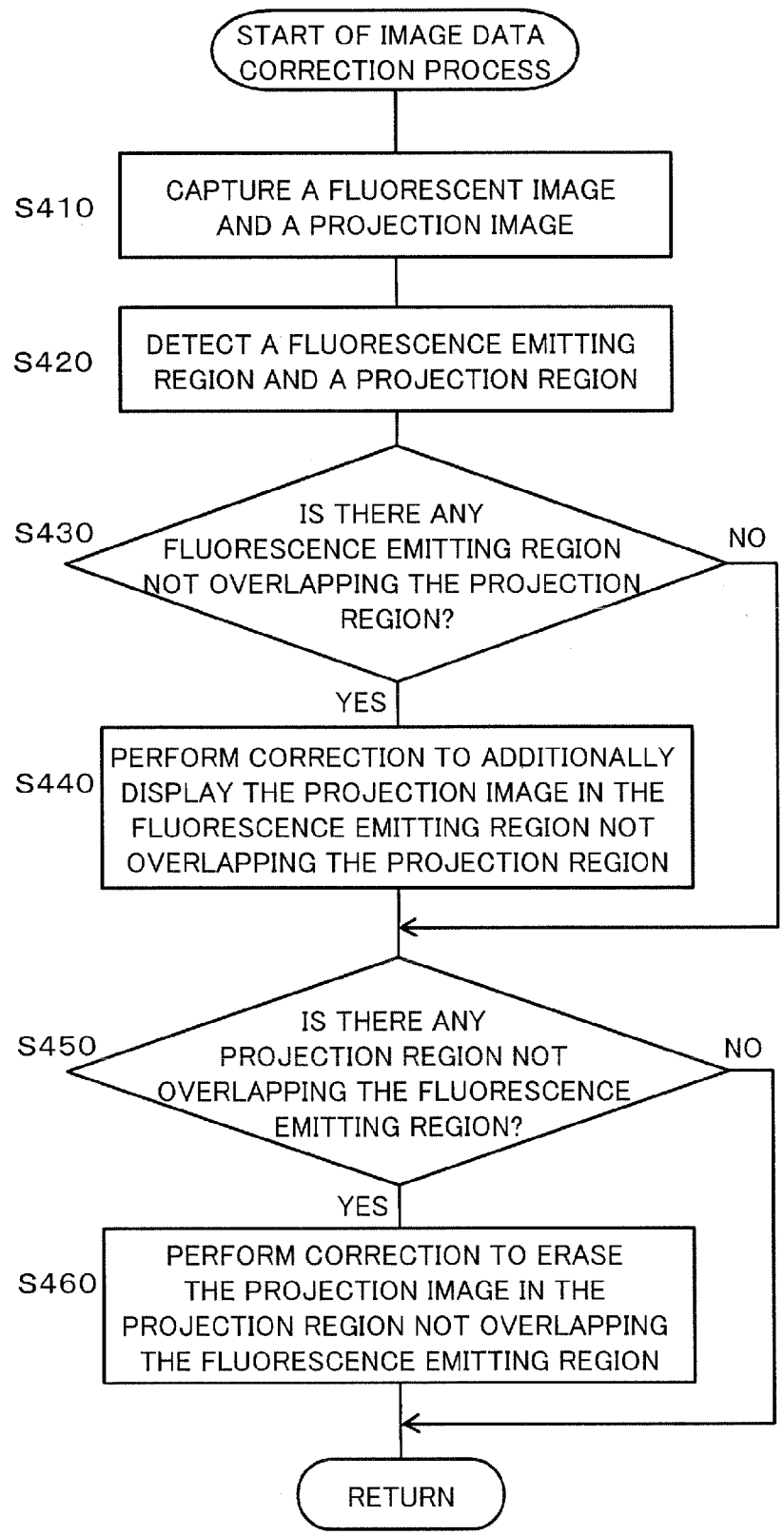
FIG. 14 is a flowchart for explaining the image data correction process of the second embodiment.

FIG. 14 is a flowchart for explaining the image data correction process (step S160). The image data correction process will be described in more detail with reference to the flowchart of FIG. 14. It is assumed in the following that, in the operative field 101, the affected part 103 emits the fluorescence and the projection image is projected onto the affected part 103.

The imaging apparatus 1 first captures the projection image from the projecting unit 3 together with the fluorescent image in the operative field 101 (step S410). The control unit 2 detects the fluorescence emitting region and the projection region in the operative field 101 based on the captured image data from the imaging apparatus 1 (step S420). Specifically, the control unit 2 detects each of the regions occupied by the fluorescence region and the projection image in the captured image data.

The control unit 2 determines whether any fluorescence emitting region that does not overlap on the projection region is present in the captured image data (step S430). When the control unit 2 determines that the fluorescence emitting region not overlapping on the projection region is present (YES at step S430), the control unit 2 corrects the image data for projection such that the projection image is additionally displayed in such a region (step S440). Specifically, the control unit 2 adds an image to the region of the image data for projection corresponding to the fluorescence emitting region that does not overlap on the projection region in the captured image data.

The control unit 2 determines whether any projection region that does not overlapping on the fluorescence emitting region is present (step S450). When the control unit 2 determines that the projection region not overlapping on the fluorescence emitting region is present (YES at step S450), the control unit 2 corrects the image data for projection to erase the projection image in such a region (step S460). Specifically, the control unit 2 erases the projection image of the region in the image data for projection corresponding to the projection region that does not overlap on the fluorescence emitting region in the captured image data.

The above process will be described specifically taking an example in FIGS. 12A to 12C. A region 33b indicated by shading therein in FIG. 12A denotes a region where the projection image 33 displays, albeit not including in the affected part 103, with deviation. FIG. 12B shows the state of the operative field 101 after the correction is made according to the above process. FIG. 12C shows the image data for projection after the correction.

In the above process, the control unit 2 determines that the region 33b indicated by the shading therein is the projection region that does not overlap on the fluorescence emitting region (YES at step S450) and corrects image data 333 for projection to erase the shaded region 33b (step S460) Specifically, the control unit 2 erases the image of the region D33b corresponding to the region 33b in the image of the affected part in the image data 333 for projection.

The blackened region 33a of the projection image 33 shown in FIG. 12A is the region having the fluorescence emitting region and the projection region overlapping therein on each other, and the control unit 2 therefore maintains the region 33a of the projection image as is displayed. Specifically, the control unit 2 maintains the image of a region D33a corresponding to the region 33a in the image of the affected part in the image data D33 for projection.

The above process causes the figure of the image of the affected part that is a circle before the correction to be changed to an oval-like shape represented by the region D33a in the image data 333 for projection. The image of the region D33a in the image data D33 for projection is projected from the projecting unit 3 disposed inclined against the operative field 101 and, thereby, the figure of the projection image becomes a circle.

Thereby, as shown in FIG. 12B, the region 33b is erased that is displayed in the region deviated from the affected part 103 in the projection image 33, and only the region 33a is maintained that matches with the affected part 103. In this manner, the image data correction process in this embodiment can resolve the deviation of the projection image.

Although the imaging unit 12 is configured to be able to detect both of the visual light and the fluorescence in this embodiment, the imaging unit 12 may be configured to include an imaging unit to detect only the visual light and an imaging unit to detect only the fluorescence separately from each other, for performing the above process. With this configuration, the fluorescent image and a projected image can each be processed as an independent image and a signal process can therefore be performed at a high speed and with high precision to distinguish the fluorescence emitting region from the outside of the fluorescence emitting region, and the projection region from the outside of the projection region.

Exemplary application of the image data correction process for the case where the affected part moves with elapse of time will be described with reference to FIGS. 15A to 15C.

Figure 15A:
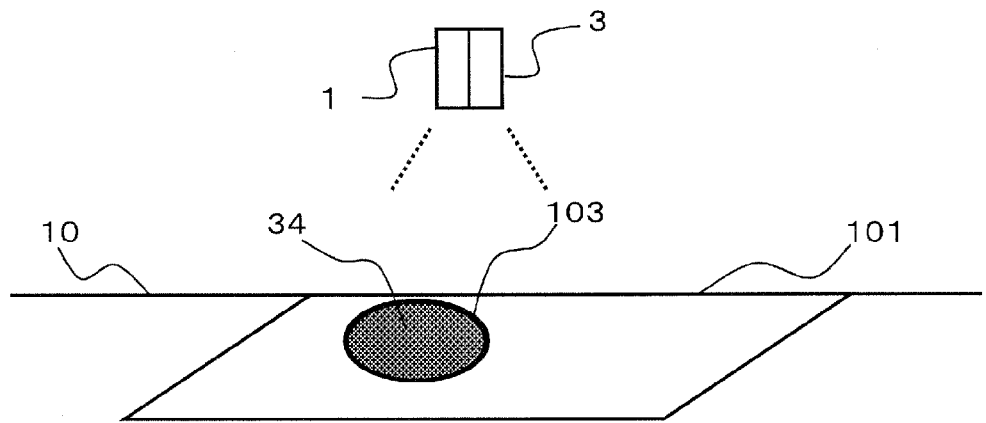
FIG. 15A is a diagram showing a moving example of an affected part in the medical operation support system of the second embodiment.
Figure 15B:
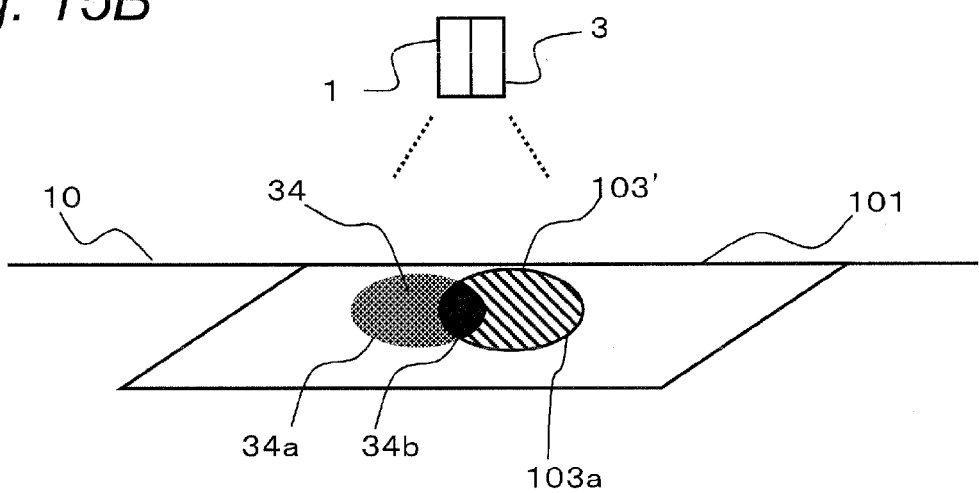
FIG. 15B is a diagram showing an example of the moved affected part in the medical operation support system of the second embodiment.
Figure 15C:
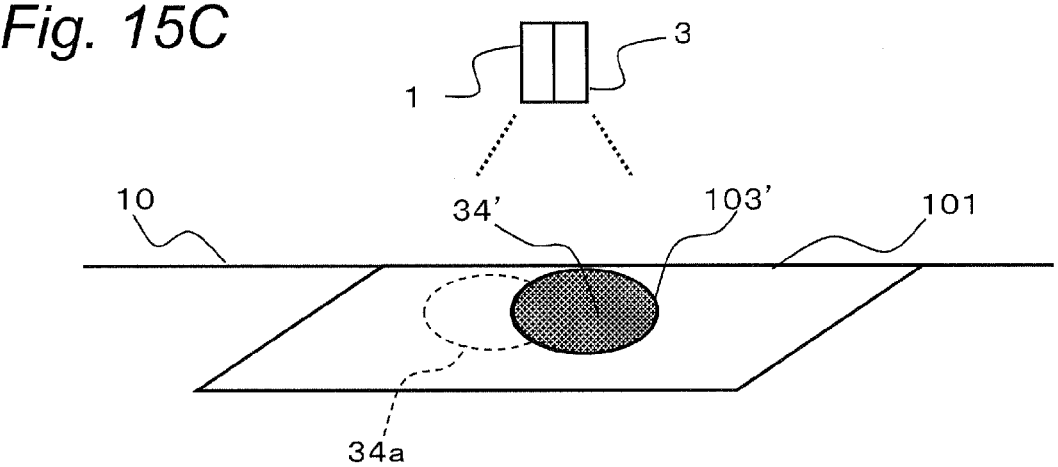
FIG. 15C is a diagram of an example of a projection image corrected in the medical operation support system of the second embodiment.

In the example shown in FIGS. 15A to 15C, the imaging apparatus 1 and the projecting unit 3 are disposed in parallel and adjacent to each other above the operative field 101. FIG. 15A shows the state where a projection image 34 is projected with the position of the projection image 34 from the projecting unit 3 and the position of the affected part 103 matching with each other.

FIG. 15B shows the state where the affected part 103 moves from the state of the operative field 101 shown in FIG. 15A. As shown in FIG. 15B, the move of the affected part 103 causes deviation between the fluorescence emitting region of an affected part 103' after the move and the projection region of the projection image 34 from the projecting unit 3. In response to this, the control unit 2 of the medical operation support system 200 performs the image data correction process as follows.

A region 103a indicated by a slashed portion in FIG. 15B denotes a region on the affected part 103 as well as the region where the projection image 34 does not displayed. The control unit 2 corrects the image data for projection such that the projection image is displayed in the region 103a (step S440).

A region 34a indicated by a shaded portion in FIG. 15B denotes a region not emitting any fluorescence as well as the region where the projection image 32 displays due to the deviation. The control unit 2 corrects the image data for projection such that the display of the projection image 34 is stopped in the region 34a (step S460).

The projection image of a region 34b indicated by a blackened portion in FIG. 15B is projected onto the affected part 103. The control unit 2 does not change and maintains the image in a region corresponding to the region 34b in the image data for projection (a left column in the FIG. 13(*a*) top row).

Performing of the image data correction process enables the affected part 103' after the move and a projection image 34' to match with each other, and the deviation of the display caused by the projecting unit 3 to be resolved as shown in FIG. 15C.

As above, the difference is detected between the fluorescent image of the affected part and the projection image of the projecting unit 3 and, thereby, the image of the affected part can be projected at the proper position even when the surface figure or a move of the affected part causes any deviation.

2-3. Effects and the Like

As above, in this embodiment, the medical operation support system 200 includes the light source 11, the imaging unit 12, the control unit 2, and the projecting unit 3. The light source 11 applies the excitation light beam having the predetermined wavelength. The imaging unit 12 captures the affected part 103 in the operative field 101 that is the subject to which the excitation light beam is applied. The control unit 2 generates the image data for projection based on the captured image data captured by the imaging unit 12. The projecting unit 3 projects onto the operative field 101 the projection image based on the image data for projection. On the operative field 101, the imaging unit 12 captures the projection image together with the fluorescent image of the fluorescence emitting region responding to the excitation light beam. The control unit 2 corrects the image data for projection according to the difference between the fluorescent image captured by the imaging unit 12 and the projection image.

According to the above configuration, the medical operation support system 200 can reduce the deviation of the projection image and can more accurately present the region of the affected part 103. The doctor, etc., therefore, can more easily recognize the accurate state of the subject in the image of the subject projected onto the actual subject. The correction of the image data for projection performed according to the detected difference enables reduction of the throughput of the control unit 2 in the correction process.

The control unit 2 corrects the image data for projection to additionally display the projection image in the fluorescence emitting region 103a which responds to the light beam having the predetermined wavelength and does not overlap the projection region onto which the projection image is projected. The control unit 2 corrects the image data for projection to erase the projection image in the projection region 34a which does not overlap the fluorescence emitting region. This process enables reduction of the throughput of the control unit 2 in the correction process.

In this embodiment, the subject by the imaging unit 12 is the affected part 103 of the patient 10, however, the subject is not limited to a human body and may be, for example, an affected part of a creature whose body has a fluorescent substance administered therein that responds to a predetermined wavelength of a light beam.

In the second embodiment, the examples have been described that the deviated projection image is corrected for the cases where the imaging apparatus 1 and the projecting unit 3 are disposed at positions different from each other and where the affected part 103 moves during the medical operation. The image data correction process in this embodiment is however applicable also to the case where the projection image is deviated due to the surface figure of the affected part 103. When the projection image is deformed due to the three-dimensional surface figure of the affected part and the fluorescence emitting region and the projection region are deviated from each other, the image data correction process in this embodiment can resolve the deformation of the projection image.

In the process of step S130A in the generating process of the projection image in this embodiment, similarly to the first embodiment, the control unit 2 may perform a process of adjusting the magnification ratio of enlarging or shrinking and a rotation angle of the image data for projection to match the size and/or the orientation of the projection image with the region emitting the fluorescence in the operative field 101. The control unit 2 may match the position of the fluorescence emitting region of the affected part and the position of the projection image in the captured image data based on the visual light image of the captured image data.

(Third Embodiment)

A third embodiment will be described. Whereas the image of the affected part of the patient is projected and its image data for projection is corrected in the second embodiment, an image of a medical device is projected and its image data for projection is corrected in this embodiment.

The medical operation support system according to this embodiment will be described without arbitrarily again describing the configurations and operations same as those of the medical operation support systems 100, 200 according respectively to the first and the second embodiments.

The medical operation support system according to this embodiment is configured similarly to the medical operation support system 200 according to the second embodiment (see FIG. 10). The medical operation support system according to this embodiment performs the generating process of the projection image same as in the second embodiment employing a medical device as the subject by the imaging unit 1 and the object in the image to be projected by the projecting unit 3 (see FIG. 11).

In the generating process of the projection image in this embodiment, the control unit 2 extracts the fluorescent image of the medical device and generates the image data for projection indicating the figure of the extracted fluorescent image (step S130A). The control unit 2 may generate the image data for projection by using the same process as the image data generating process (step S130) in the first embodiment (see FIG. 8). In this case, the medical operation support system according to this embodiment further includes the memory 4 same as that of the medical operation support system 100 according to the first embodiment.

The control unit 2 performs the image data correction process same as in the second embodiment for the image data for projection indicating the figure of the medical device generated as above (step S160). At this step, the control unit 2 detects the difference between the projection image presenting the figure of the medical device and the fluorescent image of the medical device 20, and corrects the image data for projection corresponding to the difference.

Thereby, the deviation can be resolved between the position of the projection image presenting the figure of the medical device and the position of the region caused to emit the fluorescence by the medical device, and the user can visually recognize more accurately the position of the medical device. The frequency of newly generating the image data for projection can be reduced and the throughput of the control unit 2 can be reduced by repeatedly correcting the image data for projection that is once generated.

(Other Embodiments)

As described above, the first to third embodiments have been described as an exemplification of the technology disclosed in the present application. However, the technology in the present disclosure can also be applied to an embodiment in which an alteration, substitution, addition, or omission or the like has been implemented as appropriate without restriction to the first or second embodiment. Furthermore, it is also possible to combine the constituent elements described in the aforementioned the first embodiment to constitute a new embodiment.

Accordingly, examples of other embodiments are given hereinafter.

The description has been made taking the example of the medical use such as that for a medical operation, etc., in each of the first to the third embodiments, but the present invention is not limited to this. The present invention is applicable to the case where operation of work is required for an object whose change of the state cannot be checked by visual observation such as the case in, for example, a construction site, a mining site, a building site, or a plant to process a material.

Specifically, instead of the medical device of the first and the third embodiments, a fluorescent substance is applied on the surface of, is mixed by kneading in, or is poured into an object whose change of the state cannot be checked by visual observation in a construction site, a mining site, a building site, a plant to process a material, etc. to form an object to be captured which is the subject by the imaging unit 12. Concurrently, the figure information on the figure of the object is stored in the memory 4 and, thereby, the present invention is applicable similarly to the first and the third embodiments.

In the first embodiment, the pieces of image data 51 to 54 of the surgical instruments stored in the memory 4 have been exemplified. The memory 4 however may have pieces of image data stored therein of medical devices including the surgical instruments. In this case, the image database 41 and the feature value data 42 may be configured concerning the pieces of image data of the medical devices similarly to the first embodiment. Thereby, the sort of the medical device can be determined not limiting to the surgical instrument.

In the first embodiment, the image database 41 may have the image data 53 of the MERCI stored therein except that of the filament 53b. Thereby, when a medical operation is performed without including the fluorescence material in the filament of the MERCI, the comparison with its fluorescent image is facilitated. For example, determination as to whether the fluorescent image presents the MERCI or not is easily performed by comparing the degree of similarity between the fluorescent image of the captured image data and the helical figure of the loop wire. Further, image data of the MERCI without the filament may be used as the projection image regardless of the presence or the absence of the fluorescence material in the filament of the MERCI. In this manner, the image data of a partial figure of each of the medical devices may be stored in the memory 4.

The pieces of figure information stored in the memory 4 may be, for example, pieces of image data acquired in advance by capturing by the imaging apparatus 1. Thereby, more pieces of image data indicating the actually used instruments can be projected.

The figure information is the image data indicating the figure of a medical device in the first embodiment, however, the figure information may be image data on an object not only limited to the medical device but also having a predetermined figure. The image data on the object having the predetermined figure is not limited to the image data on the object itself such as the medical device. The figure information may be image data schematically indicating the object and may be, for example, a diagram depicting the object or a mark such as an arrow.

In the first embodiment, the control unit 2 performs the process of adjusting the magnification ratio and the rotation angle for the image data whose degree of similarity is the highest, based on the captured image data. The method of adjusting the magnification ratio and/or the rotation angle of the projection image is not limited to the above. For example, the control unit 2 may adjust the magnification ratio and the angle relative to the visual light image of the operative field 101 as the criterion that is captured by the imaging apparatus 1, or may install in advance a fluorescent marker in the vicinity of the operative field 101 and may adjust the magnification ratio and the rotation angle relative to this fluorescent marker as the criterion. The control unit 2 may generate the image data for projection reflecting thereon the adjustment of the magnification ratio and/or the rotation angle based on these criteria, or may control the optical system such as a lens of the projecting unit 3.

In the first to the third embodiments, the control unit 2 generates the image data for projection based on the captured image data such that the position of the fluorescent image on the surface of the affected part and the position of the projection image match with each other. Not limiting to this, the control unit 2 however may change the capturing position such that the position of the region emitting the fluorescence on the surface of the subject and the position of the projection image match with each other. For example, the control unit 2 may control the projecting unit 3 to change the projecting position of the projection image.

In the first to the third embodiments, the control unit 2 causes the position of the fluorescent image on the surface of the affected part and the position of the projection image to match with other with reference to the fluorescent image of the medical device in the captured image data. The reference for the alignment of the projection image is however not limited to this. For example, the visual light image of the operative field 101 captured by the imaging apparatus 1 may be used as the reference, or a fluorescent marker may be installed in advance in the vicinity of the operative field 101 and this fluorescent marker may be used as the reference.

In the first embodiment, the projection image is produced for one medical device and is projected. The control unit 2 may however compare the fluorescent image with plural pieces of figure information at the same time. Thereby, when plural sorts of surgical instrument are concurrently inserted in the body of the patient 10, each of the medical devices can be identified.

In the image data generating process in the first embodiment, the control unit 2 generates the image data for projection by replacing the fluorescent image of the captured image data with the image by the image data that is determined to be similar. The control unit 2 may however generate the image data for projection by referring to the determined image data and correcting the figure of the unclear fluorescent image in the captured image data.

In the first embodiment, the control unit 2 determines the sort of the medical device using the feature value data 42 stored in the memory 4. The control unit 2 may however directly determine the degree of similarity between the pieces of figure information on the plural sorts of medical device stored in the image database 41 and the fluorescent image without determining the sort of the medical device using the feature value data 42. In this case, the feature value data 42 does not need to be stored in the memory 4 and the amount of data retained in the memory 4 can therefore be reduced. Not only the sorts of the medical devices but also the data on feature values for each of the medical devices differing in the orientation and the figure from each other may be used as the feature value data 42. Thereby, in the image database 41, the figure information to be compared with the fluorescent image can further be narrowed down.

In the first to the third embodiments, the imaging unit 12 is configured to be able to detect all the kinds of lights of the visual light, the fluorescence, and the excitation light. The imaging unit 12 however only has to be configured to be able to detect at least the fluorescence. For example, the imaging unit 12 may be configured in combination with a camera capable of detecting only the visual light and the fluorescence, or may be configured by a camera capable of detecting only the fluorescence.

Though indocyanine green is exemplified as the photo-sensitive substance in the first to the third embodiments, another photo-sensitive substance may be used. For example, porphyrin, luciferin, or AkaLumine (a registered trademark) may be used. In this case, the light source 11 applies an excitation light beam in the excitation wavelength band for each of the photo-sensitive substances and the imaging unit 12 detects a fluorescent image in the wavelength band of the fluorescence emission of each of the photo-sensitive substance.

As above, the embodiments have been described as examples of the technique in this disclosure. To do this, the accompanying drawings and the detailed description have been provided.

The components shown in the accompanying drawings and described in the detailed description may therefore include not only the components essential for solving the problem but also the components not essential for solving the problem, to exemplify the technique. It should not therefore be readily recognized that those non-essential components are essential based on the fact that those non-essential components are depicted in the accompanying drawings and described in the detailed description.

The embodiments are to exemplify the technique in this disclosure and various changes, replacements, additions, omissions, etc., can be made to the embodiments within the scope of claims or a scope equivalent thereto.

Industrial Applicability

The projection system in this disclosure is applicable to the case where operation of work is required for an object whose change of the state cannot be checked by visual observation such as a medical use or a use in, a construction site, a mining site, a building site, or a plant to process a material.

The invention claimed is:

1. A projection system comprising:
   a light source for applying a light beam having a predetermined wavelength;
   an imaging unit for capturing a subject to which the light beam having the predetermined wavelength is applied;
   a control unit for generating image data for projection based on the image captured by the imaging unit;
   a storage unit for storing plural pieces of figure information each representing image data of an object having a predetermined figure; and
   a projecting unit for projecting, onto the subject, a projection image based on the image data for projection, wherein
   the control unit
   selects a piece of figure information from the plural pieces of figure information stored in the storage unit, based on a degree of similarity with an image of a region responding to the light beam having the predetermined wavelength captured by the imaging unit, and
   generates the image data for projection such that an image including a figure indicated by the selected piece of figure information is projected onto the region responding to the light beam having the predetermined wavelength.

2. The projection system according to claim 1, wherein the control unit generates the image data for projection by replacing the image of the region responding to the light beam having the predetermined wavelength with an image of the object represented by the selected piece of the figure information.

3. The projection system according to claim 1, wherein the control unit generates the image data for projection by correcting a figure of the image of the region responding to the light beam having the predetermined wavelength based on the selected piece of the figure information.

4. The projection system according to claim 1, wherein the control unit selects the piece of figure information from the plural pieces of figure information stored in the storage unit,
based on the degree of similarity between each of figures represented by the stored plural pieces of the figure information and the figure of the image of the region responding to the light beam having the predetermined wavelength.

5. The projection system according to claim 1, wherein the control unit
adjusts a magnification ratio and/or a rotation angle of the image data for projection to match a size and/or an orientation of the region responding to the light beam having the predetermined wavelength on the subject.

6. The projection system according to claim 1, wherein the control unit
causes the projecting unit to project the projection image to match a position of the region responding to the light beam having the predetermined wavelength and a position of the region of the projection image with each other on the subject.

7. The projection system according to claim 1, wherein the storage unit stores the plural pieces of figure information each representing image data of a medical device.

8. The projection system according to claim 1, wherein the subject includes an object to be captured which a fluorescent substance responding to the light beam having the predetermined wavelength is applied thereon, is kneaded therein, or is poured therein.

* * * * *